US010105325B2

(12) United States Patent
Miller et al.

(10) Patent No.: US 10,105,325 B2
(45) Date of Patent: Oct. 23, 2018

(54) TREATMENT OF PERVASIVE DEVELOPMENTAL DISORDERS WITH REDOX-ACTIVE THERAPEUTICS

(71) Applicant: BioElectron Technology Corporation, Mountain View, CA (US)

(72) Inventors: Guy M. Miller, Monte Sereno, CA (US); Viktoria Kheifets, Mountain View, CA (US)

(73) Assignee: BIOELECTRON TECHNOLOGY CORPORATION, Mountain View, CA (US)

( * ) Notice: Subject to any disclaimer, the term of this patent is extended or adjusted under 35 U.S.C. 154(b) by 0 days.

(21) Appl. No.: 15/208,549

(22) Filed: Jul. 12, 2016

(65) Prior Publication Data
US 2017/0157065 A1 Jun. 8, 2017

Related U.S. Application Data

(60) Continuation of application No. 14/605,937, filed on Jan. 26, 2015, now Pat. No. 9,399,612, which is a continuation of application No. 14/155,288, filed on Jan. 14, 2014, now Pat. No. 8,969,420, which is a division of application No. 13/651,330, filed on Oct. 12, 2012, now Pat. No. 8,653,144, which is a division of application No. 12/555,700, filed on Sep. 8, 2009, now Pat. No. 8,314,153.

(60) Provisional application No. 61/191,696, filed on Sep. 10, 2008.

(51) Int. Cl.
A61K 31/122 (2006.01)
A61K 31/05 (2006.01)
A23L 33/10 (2016.01)
A23L 33/00 (2016.01)

(52) U.S. Cl.
CPC ............ A61K 31/122 (2013.01); A23L 33/10 (2016.08); A23L 33/40 (2016.08); A61K 31/05 (2013.01); A23V 2002/00 (2013.01)

(58) Field of Classification Search
CPC .............................. A61K 31/122; A61K 31/05
See application file for complete search history.

(56) References Cited

U.S. PATENT DOCUMENTS

| | | |
|---|---|---|
| 2,398,418 A | 4/1946 | Fieser |
| 2,856,414 A | 10/1958 | Robeson et al. |
| 3,071,512 A | 1/1963 | Feldmann |
| 3,406,188 A | 10/1968 | Fletcher |
| 3,705,239 A | 12/1972 | Gregory |
| T917,001 I4 | 12/1973 | Anderson, Jr. et al. |
| 3,849,453 A | 11/1974 | Morrimoto et al. |
| 3,896,153 A | 7/1975 | Sato et al. |
| 3,909,376 A | 9/1975 | Degner |
| 3,957,836 A | 5/1976 | Morimoto et al. |
| 4,127,608 A | 11/1978 | Olson et al. |
| 4,153,614 A | 5/1979 | Barner et al. |
| 4,185,154 A | 1/1980 | Olson et al. |
| 4,201,726 A | 5/1980 | Olson et al. |
| 4,201,879 A | 5/1980 | Barner et al. |
| 4,234,490 A | 11/1980 | Barner et al. |
| 4,243,598 A | 1/1981 | Olson et al. |
| 4,310,465 A | 1/1982 | Olson et al. |
| 4,388,312 A | 6/1983 | Terao et al. |
| 4,393,075 A | 7/1983 | Terao et al. |
| 4,436,753 A | 3/1984 | Imada et al. |
| 4,491,594 A | 1/1985 | Ogawa et al. |
| 4,495,104 A | 1/1985 | Imada et al. |
| 4,559,177 A | 12/1985 | Okutani et al. |
| 4,559,407 A | 12/1985 | Barner et al. |
| 4,592,867 A | 6/1986 | Yu et al. |
| 4,599,232 A | 7/1986 | Bertelli |
| 4,617,317 A | 10/1986 | Bennet |
| 4,694,090 A | 9/1987 | Shiono et al. |
| 4,804,539 A | 2/1989 | Guo et al. |
| 4,814,346 A | 3/1989 | Albert et al. |
| 4,818,441 A | 4/1989 | Imada et al. |
| 4,831,265 A | 5/1989 | Watanabe et al. |
| 4,883,658 A | 11/1989 | Holly |
| 4,914,088 A | 4/1990 | Glonek et al. |
| 5,057,514 A | 10/1991 | Tatsuoka et al. |
| 5,059,627 A | 10/1991 | Goto et al. |
| 5,075,104 A | 12/1991 | Gressel et al. |
| 5,157,132 A | 10/1992 | Tan et al. |
| 5,179,092 A | 1/1993 | Tatsuoaka et al. |

(Continued)

FOREIGN PATENT DOCUMENTS

| | | |
|---|---|---|
| CA | 2430415 | 6/2002 |
| CN | 1441793 | 9/2003 |

(Continued)

OTHER PUBLICATIONS

Adelwohrer, C. et al. (2005, e-pub. Aug. 2, 2005). "Novel Tocopheryl Compounds XX. 1,3,8-Trioxaphenanthrenes Derived from y-Tocopherol," Tetrahedron 61:9070-9074.

Al-Gadani, Y. et al. (2009, e-pub. Mar. 21, 2009). "Metabolic Biomarkers Related to Oxidative Stress and Antioxidant Status in Saudi Autistic Children," Clinical Biochemistry 42(1011):1032-1040.

(Continued)

Primary Examiner — Jennifer M Kim
(74) Attorney, Agent, or Firm — Squire Patton Boggs (US) LLP

(57) ABSTRACT

Methods of treating or suppressing pervasive developmental disorders (PDDs) including; autistic disorder, Asperger's syndrome, childhood disintegrative disorder (CDD), Rett's disorder, and PDD-not otherwise specified (PDD-NOS) or attention deficit/hyperactivity disorder (ADHD) comprising administering to a subject in need thereof a therapeutically effective amount of one or more compounds as disclosed herein.

20 Claims, No Drawings

(56) References Cited

U.S. PATENT DOCUMENTS

| | | |
|---|---|---|
| 5,180,742 A | 1/1993 | Terao et al. |
| 5,190,618 A | 3/1993 | Top et al. |
| 5,210,239 A | 5/1993 | Abe et al. |
| 5,229,385 A | 7/1993 | Terao et al. |
| 5,278,151 A | 1/1994 | Korb et al. |
| 5,288,752 A | 2/1994 | Tatsuoka et al. |
| 5,292,768 A | 3/1994 | Tatsuoka et al. |
| 5,294,607 A | 3/1994 | Glonek et al. |
| 5,304,658 A | 4/1994 | Terao et al. |
| 5,371,108 A | 12/1994 | Korb et al. |
| 5,547,827 A | 8/1996 | Chen et al. |
| 5,600,029 A | 2/1997 | Kaneko et al. |
| 5,801,159 A | 9/1998 | Miller et al. |
| 5,846,988 A | 12/1998 | Hellberg |
| 5,874,461 A | 2/1999 | De Chaffoy De Courcelles et al. |
| 5,886,030 A | 3/1999 | Maniar |
| 5,969,133 A | 10/1999 | Ono et al. |
| 5,981,601 A | 11/1999 | Nagley et al. |
| 6,011,046 A | 1/2000 | Ohkawa et al. |
| 6,045,826 A | 4/2000 | Borowy-Borowski et al. |
| 6,083,982 A | 7/2000 | Wechter et al. |
| 6,133,278 A | 10/2000 | Terao et al. |
| 6,133,322 A | 10/2000 | Rustin et al. |
| 6,136,859 A | 10/2000 | Henrikesen |
| 6,150,402 A | 11/2000 | Wechter et al. |
| 6,187,811 B1 | 2/2001 | Lane |
| 6,232,060 B1 | 5/2001 | Miller et al. |
| 6,239,171 B1 | 5/2001 | Lane et al. |
| 6,271,266 B1 | 8/2001 | Miyamoto et al. |
| 6,297,281 B1 | 10/2001 | Chabier de Lassauniere et al. |
| 6,300,377 B1 | 10/2001 | Chopra |
| 6,331,532 B1 | 12/2001 | Muprhy et al. |
| 6,342,516 B1 | 1/2002 | Umeda et al. |
| 6,395,915 B1 | 5/2002 | Bellafiore et al. |
| 6,417,233 B1 | 7/2002 | Sears et al. |
| 6,426,362 B1 | 7/2002 | Miller et al. |
| 6,433,199 B1 | 8/2002 | Ono et al. |
| 6,454,184 B1 | 9/2002 | Merkel et al. |
| 6,472,378 B2 | 10/2002 | Von Borstel |
| 6,528,042 B1 | 3/2003 | Brown et al. |
| 6,545,184 B1 | 4/2003 | Lipshutz |
| 6,562,372 B1 | 5/2003 | Yokoi et al. |
| 6,608,196 B2 | 8/2003 | Wang et al. |
| 6,653,346 B1 | 11/2003 | Wang et al. |
| 6,656,358 B2 | 12/2003 | May et al. |
| 6,740,338 B1 | 5/2004 | Chopra |
| 6,764,768 B2 | 7/2004 | Mrksich et al. |
| 6,838,104 B2 | 1/2005 | Jacobs |
| 6,852,895 B2 | 2/2005 | Lipshutz et al. |
| 6,977,270 B2 | 12/2005 | Baldenius et al. |
| 7,034,054 B2 | 4/2006 | Miller et al. |
| 7,038,067 B2 | 5/2006 | Couladouros et al. |
| 7,078,541 B2 | 7/2006 | Boddupalli et al. |
| 7,118,688 B2 | 10/2006 | Mora-Gutierrez et al. |
| 7,119,117 B2 | 10/2006 | Beinlich et al. |
| 7,393,662 B2 | 7/2008 | Heavner et al. |
| 7,470,798 B2 | 12/2008 | Wang et al. |
| 7,491,312 B2 | 2/2009 | Gilat et al. |
| 7,514,461 B2 | 4/2009 | Wang et al. |
| 7,718,176 B2 | 5/2010 | Heavner et al. |
| 7,875,607 B2 | 1/2011 | Wang et al. |
| 7,968,746 B2 | 6/2011 | Jankowski et al. |
| 8,044,097 B2 | 10/2011 | Wang et al. |
| 8,106,223 B2 | 1/2012 | Wesson et al. |
| 8,182,990 B2 | 5/2012 | Mashima et al. |
| 8,314,153 B2 | 11/2012 | Miller et al. |
| 8,394,392 B2 | 3/2013 | Imahashi et al. |
| 8,519,001 B2 | 8/2013 | Jankowski et al. |
| 8,575,369 B2 | 11/2013 | Wesson et al. |
| 8,653,144 B2 | 2/2014 | Miller et al. |
| 8,716,486 B2 | 5/2014 | Hinman et al. |
| 8,716,527 B2 | 5/2014 | Hinman et al. |
| 8,791,155 B2 | 7/2014 | Wang et al. |
| 2001/0044462 A1 | 11/2001 | Hensley et al. |
| 2002/0032171 A1 | 3/2002 | Chen et al. |
| 2002/0132845 A1 | 9/2002 | Miller et al. |
| 2002/0182196 A1 | 12/2002 | McCleary |
| 2003/0022818 A1 | 1/2003 | Miller et al. |
| 2003/0119054 A1 | 6/2003 | Mrksich et al. |
| 2003/0134028 A1 | 7/2003 | Lievense |
| 2003/0144219 A1 | 7/2003 | Phinney et al. |
| 2003/0158237 A1 | 8/2003 | Saragovi et al. |
| 2004/0043103 A1 | 3/2004 | McCleary |
| 2004/0156871 A1 | 8/2004 | Borowy-Borowski et al. |
| 2004/0241628 A1 | 12/2004 | Thomas et al. |
| 2005/0043553 A1 | 2/2005 | Smith et al. |
| 2005/0049227 A1 | 3/2005 | Old et al. |
| 2005/0065099 A1 | 3/2005 | Walkinshaw et al. |
| 2005/0065150 A1 | 3/2005 | Wang et al. |
| 2005/0186518 A1 | 8/2005 | Masskasky et al. |
| 2005/0203066 A1 | 9/2005 | Von Borstel |
| 2005/0222218 A1 | 10/2005 | Meier et al. |
| 2005/0234248 A1 | 10/2005 | Kossler et al. |
| 2005/0256186 A1 | 11/2005 | Morishige |
| 2006/0002885 A1 | 1/2006 | Mielke et al. |
| 2006/0241174 A1 | 10/2006 | Mueller et al. |
| 2006/0281809 A1 | 12/2006 | Miller et al. |
| 2007/0066541 A1 | 3/2007 | Hughes et al. |
| 2007/0072943 A1 | 3/2007 | Miller et al. |
| 2007/0135335 A1 | 6/2007 | Collier et al. |
| 2007/0180544 A1 | 8/2007 | Palmer et al. |
| 2007/0225261 A1 | 9/2007 | Miller et al. |
| 2007/0248590 A1 | 10/2007 | Milne et al. |
| 2008/0093985 A1 | 4/2008 | Morishita et al. |
| 2008/0213239 A1 | 9/2008 | Morris |
| 2008/0221050 A1 | 9/2008 | Mashima |
| 2009/0036542 A1 | 2/2009 | Luu et al. |
| 2009/0060981 A1 | 3/2009 | Chauhan |
| 2009/0162890 A1 | 6/2009 | Gilat et al. |
| 2009/0163529 A1 | 6/2009 | Gilat et al. |
| 2009/0192179 A1 | 7/2009 | Wang et al. |
| 2009/0291092 A1 | 11/2009 | Miller et al. |
| 2010/0010100 A1 | 1/2010 | Hinman et al. |
| 2010/0029784 A1 | 2/2010 | Hinman et al. |
| 2010/0056429 A1 | 3/2010 | Miller et al. |
| 2010/0063161 A1 | 3/2010 | Miller et al. |
| 2010/0093845 A1 | 4/2010 | Wong et al. |
| 2010/0222436 A1 | 9/2010 | Miller et al. |
| 2010/0249032 A1 | 9/2010 | Heavner et al. |
| 2010/0266591 A1 | 10/2010 | Bugelski et al. |
| 2010/0273892 A1 | 10/2010 | Miller et al. |
| 2010/0273894 A1 | 10/2010 | Miller |
| 2011/0027397 A1 | 2/2011 | Theoharides |
| 2011/0046156 A1 | 2/2011 | Miller |
| 2011/0046219 A1 | 2/2011 | Hinman et al. |
| 2011/0124679 A1 | 5/2011 | Hinman et al. |
| 2011/0142834 A1 | 6/2011 | Miller |
| 2011/0172312 A1 | 7/2011 | Miller et al. |
| 2011/0183019 A1 | 7/2011 | Theoharides |
| 2011/0207828 A1 | 8/2011 | Miller et al. |
| 2011/0218208 A1 | 9/2011 | Hinman et al. |
| 2011/0263720 A1 | 10/2011 | Paisley et al. |
| 2011/0269776 A1 | 11/2011 | Miller |
| 2012/0088783 A1 | 4/2012 | Wang et al. |
| 2012/0101169 A1 | 4/2012 | Hawi |
| 2012/0122969 A1 | 5/2012 | Miller |
| 2012/0130093 A1 | 5/2012 | Wesson et al. |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |
| 2013/0289034 A1 | 10/2013 | Jankowski et al. |
| 2013/0345312 A1 | 12/2013 | Jankowski et al. |
| 2014/0031432 A1 | 1/2014 | Jankowski et al. |
| 2014/0031433 A1 | 1/2014 | Miller et al. |
| 2014/0039065 A1 | 2/2014 | Miller |
| 2014/0206772 A1 | 7/2014 | Miller et al. |
| 2014/0221674 A1 | 8/2014 | Wesson et al. |
| 2014/0243424 A1 | 8/2014 | Mollard et al. |
| 2014/0249160 A1 | 9/2014 | Miller et al. |
| 2014/0249332 A1 | 9/2014 | Mollard |
| 2014/0275054 A1 | 9/2014 | Hinman et al. |
| 2015/0057363 A1 | 2/2015 | Miller et al. |

(56) References Cited

U.S. PATENT DOCUMENTS

| | | | |
|---|---|---|---|
| 2015/0216820 A1 | 8/2015 | Miller et al. | |
| 2015/0218079 A1 | 8/2015 | Shrader et al. | |
| 2016/0024085 A1 | 1/2016 | Hinman et al. | |
| 2016/0115141 A1 | 4/2016 | Hinman et al. | |

FOREIGN PATENT DOCUMENTS

| | | |
|---|---|---|
| DE | 38 18 696 | 3/1989 |
| EP | 0025692 A1 | 3/1981 |
| EP | 0065368 A1 | 11/1982 |
| EP | 0107806 A1 | 5/1984 |
| EP | 0107806 B1 | 5/1984 |
| EP | 0 134 198 | 3/1985 |
| EP | 0326987 A2 | 8/1989 |
| EP | 0326987 A3 | 8/1989 |
| EP | 0 619 313 | 10/1994 |
| EP | 0629400 A1 | 12/1994 |
| EP | 0 719 552 | 12/1995 |
| EP | 1 378 753 | 1/2004 |
| EP | 1611879 A1 | 1/2006 |
| FR | 1 201 200 | 12/1959 |
| FR | 75631 | 7/1961 |
| FR | 5531 | 11/1967 |
| FR | 1 536 576 | 8/1968 |
| JP | 40-9029 | 5/1965 |
| JP | 48-75564 A | 10/1973 |
| JP | 49-88862 A | 8/1974 |
| JP | 52-111576 A | 9/1977 |
| JP | 52-130922 | 11/1977 |
| JP | 56-140943 | 11/1981 |
| JP | 57-050935 | 3/1982 |
| JP | 58-018374 | 2/1983 |
| JP | 58-083698 | 5/1983 |
| JP | 58-193689 | 11/1983 |
| JP | 60-28919 A | 2/1985 |
| JP | 60-056902 A | 4/1985 |
| JP | 60-197621 | 10/1985 |
| JP | 61-040236 A | 2/1986 |
| JP | 63-063674 A | 3/1988 |
| JP | 1 093 554 | 4/1989 |
| JP | 1 209 445 | 8/1989 |
| JP | 1 233 278 A | 9/1989 |
| JP | 5-11467 | 1/1993 |
| JP | 8-92151 | 4/1996 |
| JP | 2000-202297 | 7/2000 |
| JP | 2000-202297 A | 7/2000 |
| JP | 2003-64017 | 3/2003 |
| JP | 2003-64017 A | 3/2003 |
| JP | 2003-137716 | 5/2003 |
| JP | 2003-137716 A | 5/2003 |
| WO | WO 1993/24650 | 12/1993 |
| WO | WO 1998/34646 | 8/1998 |
| WO | WO 1999/38860 A1 | 8/1999 |
| WO | WO-2000/35444 A1 | 6/2000 |
| WO | WO 2000/50043 | 8/2000 |
| WO | WO 2000/78296 A2 | 12/2000 |
| WO | WO 2000/78296 A3 | 12/2000 |
| WO | WO 2001/52822 | 7/2001 |
| WO | WO 2001/92215 | 12/2001 |
| WO | WO-2002/006261 A1 | 12/2001 |
| WO | WO 2002/30419 A1 | 4/2002 |
| WO | WO 2002/34259 | 5/2002 |
| WO | WO 02/43507 A2 | 6/2002 |
| WO | WO 02/43507 A3 | 6/2002 |
| WO | WO 02/47680 A2 | 6/2002 |
| WO | WO 02/47680 A3 | 6/2002 |
| WO | WO 02/47680 A9 | 6/2002 |
| WO | WO 2002/50054 A2 | 6/2002 |
| WO | WO 2002/50054 A3 | 6/2002 |
| WO | WO 2002/067864 | 9/2002 |
| WO | WO 2003/064403 A1 | 8/2003 |
| WO | WO 2003/100986 A2 | 12/2003 |
| WO | WO 2004/003565 | 1/2004 |
| WO | WO 2004/042353 | 5/2004 |
| WO | WO 2005/000357 | 1/2005 |
| WO | WO-2005/013911 A2 | 2/2005 |
| WO | WO-2005/013911 A3 | 2/2005 |
| WO | WO 2005/019232 | 3/2005 |
| WO | WO 2005/032544 | 4/2005 |
| WO | WO 2005/033092 | 4/2005 |
| WO | WO 2005/033093 | 4/2005 |
| WO | WO 2005/105159 | 11/2005 |
| WO | WO 2006/130775 | 12/2006 |
| WO | WO 2007/095630 | 8/2007 |
| WO | WO 2008/142433 A1 | 11/2008 |
| WO | WO-2008/157747 A1 | 12/2008 |
| WO | WO 2011/041452 A2 | 4/2011 |
| WO | WO 2011/113018 A1 | 9/2011 |
| WO | WO 2012/019029 A2 | 2/2012 |
| WO | WO 2012/019029 A3 | 2/2012 |
| WO | WO 2012/019032 A1 | 2/2012 |
| WO | WO 2012/154613 A1 | 11/2012 |
| WO | WO 2012/170773 A1 | 12/2012 |
| WO | WO 2013/006736 A1 | 1/2013 |

OTHER PUBLICATIONS

Anderson et al. "No evidence for altered muscle mitochondrial function in Parkinson's disease," *Journal of Neurology, Neurosurgery, and Psychiatry*, 1993, vol. 56, pp. 477-480.

Angley, M. et al. (Sep. 2007). "Children and Autism. Part 1—Recognition and Pharmacological Management," *Australian Family Physician* 36(9):741-744.

Anonymous (Feb. 2010). "List of Publications Noting Mitochondria! Involvement in Diseases," 3 Pages.

Antalis, C.J. et al. (2006). "High Dietary Alpha Tocopherol Improves Attention Deficit/Hyperactivity (ADHD)-Like Behavior in Juvenile Spontaneously Hypertensive Rats (SHR)," *FASEB Journal* 20(5): A1002-A1003, Abstract.

Armstrong, J.S. et al. (Dec. 5, 2003). "The Coenzyme Clio Analog Decylubiquinone Inhibits the Redox-Actived Mitochondrial Permeability Transition," *The Journal of Biological Chemistry* 278(49):49079-49084.

Asgill, J.O. et al. (Jan. 4, 1978). "Chromenylation of 2-Napthol and Alkylhydroquinones: Short Synthesis of (2RS,4'R, 8'R)-.alpha.-Tocopherol (Vitamin E) and (2RS,4'R, 8TR)-(3 Tocopherol," *The Journal of the Chemical Society Chemical Communications* 1:59-60.

Asin-Cayuela, J. et al. (Jul. 30, 2004). "Fine-Tuning the Hydrophobicity of a Mitochondria-Targeted Antioxidant," *FEBS Letters* 571(1-3):9-16.

Babiroli, B. et al. (Jul. 1995). "Lipoic (Thioctic) Acid Increases Brain Energy Availability and Skeletal Muscle Performance as Shown by in Vivo 31P-MRS in a Patient with Mitochondrial Cytopathy," *Journal of Neurology* 242(7):472-477.

Boyer, P.D. (Feb. 19, 1951). "The Preparation of Reversible Oxidation Product of a-Tocopherol, a-Tocopheroxide and of Related Oxides," *Journal of the American Chemical Society* 73(2):733-740.

Briere, J-J. et al. (Apr. 16, 2004). "Quinone Analogues Regulate Mitochondrial Substrate Competitive Oxidation," *Biochemical and Biophysical Research Communications* 316(4):11381142.

Calviello, G. et al. (2003). "γ Tocopheryl Wuinone Inducs Apoptosis in Cancer Cells Via Caspase-9 Activation and Cytochrome c Release" *Carcinogenesis* 24(3):427-433.

Caplus Accession No. 169:524242, created May 12, 1984, 3 pages.
Caplus Accession No. 1967:18647, created May 12, 1984, 9 pages.
Caplus Accession No. 1969:433438, created May 12, 1984, 1 page.
Caplus Accession No. 1989:553350, created Oct. 28, 1999, 4 pages.
Caplus Accession No. 2003:166979, created Mar. 5, 2003, 5 pages.
Caplus Accession No. 2003:487787, created Jun. 27, 2003, 8 pages.
Cassels, C. (Apr. 15, 2008, updated Apr. 25, 2008). "Mitochondrial Dysfunction May Play a Role in Autism Spectrum Disorders Etiology," Medscape Press Release, located at http://www.medscape.com/viewarticle/573004, 2 pages.

Chariot, P. et al. (Apr. 1994). "Determination of the Blood Lactase: Pyruvate Ratio as a Noninvasive Test for the Diagnosis of Zidovudine Myopathy," *Arthritis & Rheumatism* 37(4):583-586.

(56) References Cited

OTHER PUBLICATIONS

Chariot, P. et al. (Jul. 1994). "Optimal Handling of Blood Samples for Routine Measurement of Lactate and Pyruvate," *Archives of Pathology & Laboratory Medicine* 118(7):695-697.

Chauhan, A. et al. (Aug. 1, 2006). "Oxidative Stress in Autism," *Pathophysiolog* 13(3):171-181.

Chez et al., "Double-Blind, Placebo-Controlled Study of L-Carnosine Supplementation in Children With Autistic Spectrum Disorders", *Journal of Child Neurology*, vol. 17, No. 11 , Nov. 2002, pp. 833-837.

Chugani, D.C. et al. (May 1999). "Evidence of Altered Energy Metabolism in Autistic Children," *Progress in Neuro-Psychopharmacology & Biological Psychiatry* 23(4):635-641.

Cohen, N. et al. (1981). "Studies on the Total Synthesis of (2R,4'R,8'R)-.alpha.-Tocopherol (Vitamin E). Stereospecific Cyclizations Leading to Optically Active Chromans," *The Journal of Organic Chemistry* 46(12):2445-2450.

Coleman, M. et al. (Mar. 1985). "Autism and Lactic Acidosis," *Journal of Autism and Developmental Disorders* 15(1):1-8.

Cressman et al. "One-Step Synthesis of Polyalkyl-2-iodo-p-benzoquinones", *Journal of Organic Chemistry*, 1966, 31 (4), pp. 1279-1281.

Dolske et al., "A Preliminary Trial of Ascorbic Acid as Supplemental Therapy for Autism", *Prog. Neum-Psychopharmacol. & DioL Psychtat*. 1993, vol. 17, pp. 765-774.

Dowd, P. et al. (Aug. 1995). "On the Mechanism of the Anticlotting Action of Vitamin E Quinone," *Proceedings of the National Academy of Science USA* 92:8171-8175.

Durckheimer, W. et al. (Oct. 20, 1964). "The Chemistry of 9-Hydroxy-.alpha.-Tocopherone, a Quinone Hemiacetal", *Journal of the American Chemical Society* 86(20):4388-4393.

Echtay, K.S. et al. (Nov. 30, 2000). "Coenzyme Q is an Obligatory Cofactor for Uncoupling Protein Function," *Nature* 408:609-613.

Erhola, M. et al. (Jun. 9, 1997). "Biomaker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.

Fabrizi, G.M. et al. (Apr. 1996). "Autosomal Dominant Limb Girdle Myopathy with Ragged-Red Fibers and Cardiomyopathy: A Pedigree Study by in Vivo 31P-MR Spectroscopy Indicating a Multisystem Mitochondrial Defect," *Jornal of the Neurological Sciences* 137(1):20-27.

Fieser, L.F. et al. (Sep. 1942). "Alkylation of Para Quinones with Acyl Peroxides," *Journal of the American Chemical Society* 64(9):2060-2065.

Filipek, P.A. et al. (Dec. 2004). "Relative Carnitine Deficiency in Autism," *Journal of Autism and Developmental Disorders* 34(6):615-623.

Fujishima, T. et al. (1996, e-pub. Sep. 23, 2006). "Synthesis of Vitamin E Analogues: Possible Active Forms of Vitamin E," *Arch. Pharm. Pharma. Med. Chem*. 329(1):27-34.

Fukunaga, K. et al. (1998). "A Simple, Rapid, Highly Sensitive and Reproducible Quantification Method for Plasma Malondialdehyde by High-Performance Liquid Chromatography," *Biomedical Chromatography* 12:300-303.

Gille, L. et al. (2001). "Effects of Tocopheryl Quinone on the Heart: Model Experiments with Xanthine Oxidase, Heart Mitochondria, and Isolted Perfused Rat Hearts," *Free Radical Biology and Medicine* 30(8):865-876.

Gille, L. et al. (2004). "Oxidized Vitamin E and Ubiquinone: Competition for Binding Sites of the Mitochondrial Cytochrome 'Complex?" *Annals of the New York Academy of Sciences* 1031:341-343.

Gille, L. et al. (2004). "Redox-Interaction of a a-Tocopheryl Quinone with Isolated Mitochondrial Cytochrome Complex," *Biochemical Pharmacolgy* 68:373-381.

Goldstein, S. et al. (Jun. 2004). "The Comorbidity of Pervasive Developmental Disorder and Attention Deficit Hyperactivity Disorder: Results of a Retrospective Chart Review," *Journal of Autism and Developmental Disorders* 34(3):329-339.

Goodhue, C.T. et al. (May 1965). "Reactions of Vitamin E with Peroxides. II. Reaction of Benzoyl Peroxide with aTocopherol in Alcohols," *Biochemistry* 4(5):854-858.

Green, J. et al. (1966) "Bond Stabilisation in Tocopherols. Part I. The Claisen Rearrangement of Allyl Tocopheryl Ethers," *Journal of the Chemical Society C*, pp. 1422-1427.

Gu et al. "Synthesis, Oxidation-Reduction Potentials and Biological Activity of 1, 4-Benzoquinone Derivatives," *Youji Huaxue*, 1991, 11(5):481-487.

Gu et al. "Synthesis and Inhibitory Activity of Bromoquinone Derivatives", *Tetrahedron*, 1990, 46 (9), pp. 3199-3210.

Gu, L-Q. et al. (1990). "Effect of Substituents of the Benzoquinone Ring on Electron-Transfer Activities of Ubiquinone Derivatives," *Biochimica et Biophysica Acta* 1015(3):482-492.

Hagio, K. et al. (Apr. 1974). "Synthesis and Reactions of 4-Dimethylsulfuranylidene-2,3,-Dioxotetrahydrofuran Derivatives." *Bulletin of the Chemical Society of Japan* 47(4):909-916.

Hattori, J. et al. (2006). "Are Pervasive Developmental Disorders and Attention Deficit/Hyperactivity Disorder Distinct Disorders?" *Brain & Development* 28:371-374.

Honda, M. et al. (Jun. 2000). "Correlation of Urinary 8-Hydroxy-2'-Deoxyguanosine (8-OHdG), a Biomaker of Oxidative DNA Damage, and Clinical Features of Hematological Disorders: A Pilot Study," *Leukemia Research* 24(6):461-468.

Hubscher, J.V. et al. (1990). "Total Synthesis of Naturally Occurring .alpha.-Tocopherol. Asymmetric Alkylation and Asymmetric Epoxidation as Means to Introduce (R)-Configuration at C(2) of the Chroman Moiety," *Helvetica Chimica Acta* 73(4-6):1068-1086 (English Translation of Abstracts Only).

Infante, J.P. (1999). "A Function for the Vitamin E Metabolite .alpha.-Tocopherol Quinone as an Essential Enzyme Cofactor for the Mitochondrial Fatty Acid Desatures," *The FEBS Letters* 446:1-5.

Inoue, S. et al. (1987). "Improved General Method of Ortho Alkylation of Phenols Using Alkyl Isopropyl Sulfide, Sulfryl Chloride, and Triethylamine. An Expedient Synthesis of Representative Oxygen Heterocycles and (2R,4'R, 8'R)-.alpha.-Tocopherol," *Journal of Organic Chemistry* 52:5495-5497.

International Preliminary Report on Patentability dated Jan. 4, 2012, for PCT Patent Application No. PCT/US2010/025447, filed on Feb. 25, 2010, one page.

International Preliminary Report on Patentability dated Mar. 15, 2011, for PCT Patent Application No. PCT/US2009/056254, filed on Sep. 8, 2009, one page.

International Search Report dated Apr. 16, 2010 for PCT Patent Application No. PCT/US2010/25447, filed on Feb. 25, 2010, 2 pages.

International Search Report dated Feb. 8, 2007, for PCT Patent Application No. PCT/US2006/036052 filed on Sep. 15, 2006, 9 pages.

International Search Report dated Nov. 12, 2009, for PCT Patent Application No. PCT/US2009/056254, filed on Sep. 8, 2009, 3 pages.

Ishizaki et al., "Usefulness of melatonin for developmental sleep and emotional/behavior disorders—studies of melatonin trial on 50 patients", *No To Hattatsu*, Sep. 1999, vol. 31, No. 5, pp. 428-437, with English abstract.

James, A.M. et al. (Jun. 3, 2005). "Interactions of Mitochondria-Targeted and Untargeted Ubiquinones with the Mitochondrial Respiratory Chain and Reactive Oxygen Species," *The Journal of Biological Chemistry* 280(22):21295-21312.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (Oct. 23, e-pub. Aug. 15, 2003). "Mitochondria-Targeted Antioxidents Protect Friedrich Ataxia Fibroblasts from Endogenous Oxidative Stress more Effectively than Untargeted Antioxidants," *The FASEB Jornal* 17(13):1972-1974.

Kabbe, H.J. et al. (1978). "Eine Neue Synthese von 3,4-Dehydro-.alpha.-Tocotrienol and Vitamin-E," *Synthesis* 888-889. (Translation of Abstract only: Chemical Abstract CAPLUS Abstract No. 1979:168774, two pages).

(56) References Cited

OTHER PUBLICATIONS

Kajiwara, M. et al. (1980). "Studies on Tocopherols II.sup.1. Convenient Synthesis of Tocopherols," *Heterocycles* 14(12):1995-1998.

Kaufman, P. et al. (Apr. 27, 2004). "Cerebral Lactic Acidosis Correlates with Neurological Impairment in MELAS," *Neurology* 62(8):1297-1302.

Kelso, G.F. et al. (Feb. 16, 2001)"Selective Targeting of a REdox-Active Ubiquinone to Mitochondria Within Cells," The Jornal of Biological Chemistry 276(7):4588-4596.

Kim, J.Y. et al. (May 2004). "Urinary 8-Hydroxy-2'-Deoxyguanosine as a Biomaker of Oxidative DNA Damage in Workers Exposed to Fine Particulates," *Environmental Health Perspectives* 112(6):666-671.

Kleijnen et al., "Niacin and Vitamin B6 in Mental Functioning: A Review of Controlled Trials in Humans", *Biol. Psychiatry*, 1991, vol. 29, pp. 931-941.

Korizis, K.N. et al. (2001). "Determination of Malondialdehyde by Capillary Electrophoresis, Application to Human Plasma and Relation of its Levels with Prematurity," *Biomedical Chromatography* 15:287-291.

Krajcovicova-Kudlackova, M. et al. (2009). "Plasma Concentrations of Selected Antioxidants in Autistic Children and Adolescents," *Bratisl lek listy* 110(4)247-250.

Kumadaki, I. et al. (1989). "Trifluoromethylation of Tocopherols," *Synthetic Communications* 19(1&2):173-177.

Larisch, B. et al. (Jul. 1996). "Reactions of Dehydroascorbic Acid with Primary Aliphatic Amines Including NaAcetyllysine," *Journal of Agricultural and Food Chemistry* 44(7):1630-1634.

Laszlo, A. et al. (1994). "Serum Serotonin, Lactate and Pyruvate Levels in Infantile Autistic Children", *Chnica Chimica Acta* 229:205-207.

Lee, P.I. (1992). "Diffusion-Controlled Matrix Systems," Chapter 3 in Treatise on Controlled Dug Delivery, Kydonieus, A. ed., *Marcel Dekker, Inc.*, New York, NY, pp. 155-197.

Lenaz, G. et al. (2000). "Mitochondrial Bioenergetics in Aging," *Biochimica et Biophysica Acta* 1459:397-404.

Liepkalns et al. "Regulation of Cell Division in a Human Glioma Cell Clone by Arachidonic Acid and a-Tocopherolquinone," *Cancer Letters*, 15 (1982) 173-178.

Lipshutz, B.H. et al. (Feb. 12, 1998). "An Expeditious Route to CoQn, Vitamins K.sub.1 and K.sub.2, and Related Allytated para-Quinones Utilizing Ni(0) Catalysis," *Tetrahedron* 54(7):1241-1253.

Lord C. et al. "Autism spectrum disorder", *Neuron* 2000 28 (2): 355-63.

Lynch, D.R. et al. (May 2002). "Near Infrared Muscle Spectroscopy in Patients with Friedreich's Ataxia," *Muscle & Nerve* 25(5):664-673.

MacKenzie, J.B. et al. (1950). "The Biological Activity of .alpha.-Tocopherylhydroquinone and .alpha.-Tocopherylquinone," *Journal of Biological Chemistry* 183(2):655-662.

Maloney, D.J. et al. (2005, e-pub. Aug. 20, 2005). "A Stereocontrolled Synthesis of .delta.-trans-Tocotrienoloic Acid," *Acid Letters* 7(19):4297-4300.

Marpat Accession No. 138:187513, 2 pages.

Matthews, P.M. et al. (Apr. 1991). "In Vivo Magnetics Resonance Spectroscopy on Brain and Muscle in a Type of Mitochondrial Encephalomyopathy (MERRF)," *Annals of Neurology* 29(4):435-438.

Mayer, H. et al. (1967). "Uber die Chemie des Vitamins E. 8. Mitteilung [1]. Die Stereochemie von Naturlichem y-Tocotrienol (Plastochromanol-3), Plastochromanol-8 and Plastochromanol-8)," *Helvetica Chimica Acta* 50(5):1376-1393, No. 139. (English Summary on pp. 1392-1393 and Chemical Abstract CAPLUS Abstract No. 1967:473698 is also included.).

Mazzini, F. et al. (2005, e-pub. Nov. 30, 2004). "Easy Route to Lebeled and Unlabeled R, R, RyTocopherol by Aryl Demethylation of a-Homologues," *Tetrahedron* 61:813-817.

McGinnis, "Oxidative Stress in Autism", *Integrative Medicine*, vol. 3, No. 6, Dec. 2004/Jan. 2005, pp. 42-57.

Monte, W. T. et al. (May/Jun. 2001). "An Efficient Process for the Synthesis of y-Arylbutanals via Copper-Mediated Grignard Coupling," *Organic Process Research & Development* 5(3):267¬269.

Mukai, K. et al. (1989). "Synthesis and Kinetic Study of Antioxidant Activity of New Tocopherol (Vitamin E) Compounds," *The Journal of Organic Chemistry*, 54(3):552-556.

Mukai, K. et al. (1989). "Synthesis and Stopped-Flow Investigation of Antioxidant Activity of Tocopherols. Finding of New Tocopherol Derivatives Having the Highest Antioxidant Activity Among Phenolic Antioxidants," *The Journal of Organic Chemistry* 54(3):557-560.

Mukai, K. et al. (19910. "Structure-Activity Relationship in the Quenching Reaction of Singlet Oxygen by Tocopherol (Vitamin E) Derivatives and Related Phenols. Finding of Linear Correlation Between the Rates of Quenching of Singlet Oxygen and Scavenging of Peroxyl and Phenoxyl Radicals in Solution," *The Journal of Organic Chemistry* 56(13):4188-4192.

Munnich, A. et al. (1992). "Clinical Aspects of Mitochondrial Disorders," *Journal of Inherited Metabolic Disease* 15(4):448-455.

Myagkov, V. "Monomolecular Films of Octadecyl-Substituted Quinone and Hydroquinone and their Charge Transfer Complexes," *Colloid Journal of the USSR, Russian Original*, 1985, vol. 47, No. 5, pp. 833-836.

Myers, S.M. et al. (Nov. 2007, e-pub. Oct. 29, 2007). "Management of Children with Autism Spectrum Disorders," *Pediatrics* 120(5):1162-1182.

Noens, I. et al. (Sep. 2006). "The ComFor: an Instrument for the Indication of Augmentative Communication in People with Autism and Intellectual Disability," *Journal of Intellectual Disability Research* 50(Part 9):621-632.

Oliveira, G. et al. (2005). "Mitochondrial Dysfunction in Autism Spectrum Disorders: a Population-Based Study," *Developmental Medicine & Child Neurology* 47:185-189.

Omura, K. (1989). "Iodine Oxidation of .alpha.-Tocopherol and Its Model Compound in Alkaline Methanol: Unexpected Isomerization of the Product Quinone Monoketals," *The Journal of Organic Chemistry* 54(8):1987-1990.

Oswald, D.P. et al. (2007). "Medication Use Among Children with Autism-Spectrum Disorders", *Journal of Child Adolescent Psychopharmacology* 17(3):348-355.

Pearce, B.C. et al. (1992). "Hypocholesterolemic Activity of Synthetic and Natural Tocotrienols," *Journal of Medicinal Chemistry* 35(20):3595-3606.

Pearce, B.C. et al. (1994). "Inhibitors of Cholesterol Biosynthesis. 2. Hypocholesterolemic and Antioxidant Activities of Benzopyran and Tetrahydronaphthalene Analogues of the Tocotrienols," *Journal of Medicinal Chemistry* 37(4):526-541.

Pelter, A. et al. (1993). "Phenolic Oxidations with Phenyliodonium Diacetate," *Journal of the Chemical Society, Perkins Transactions* 1 16:1891-1896.

Pelter, A. et al. (1997). "The Synthesis of 8a-Methoxy-2H, 6H-Chromen-6-ones and Corresponding 2H-Chromenes by a Unique Process Utilising Phenolic Oxidation," *Tetrahedron* (53(11):3879-3916.

Pileni MP, et al. (Apr. 15, 1980). "Zinc-Porphyrin Sensitized Reduction of Simple and Functional Quinones in Vesicle Systems," *Chemical Physics Letters*, vol. 71, No. 2, pp. 317-321.

Pileni, M.P. et al. (1980). "Zinc Porphyrin Sensitized Reduction of Simple and Functional Quinones in Micellar Systems," *Journal of Physical Chemistry* 84(14):1822-1825.

Pilger, A. et al. (Sep. 2001). "Longitudinal Study of Urinary 8-Hydroxy-2'-Deoxyguanosine Excretion in Healthy Adults," *Free Radical Research* 35(3):273-280.

Pilz, J. et al. (2000). "Measurement of Free and Bound Malondialdehyde in Plasma by High Performance Liquid Chromatography as the 2,4-Dinitrophenylhydrazine Derivative," *Journal of Chromatography B* 742:315-325.

Pina, I.L. et al. (Mar. 4, 2003). "Exercise and Heart Failure: A Statement From the American Heart ASsociation Committee on Exercise, Rehabilitation, and Prevention," *Circulation* 107(8):1210-1225.

Rimland, et al., The Effect of High Doses of Vitamin B6 on Autistic Children: A Double-Blind Crossover Study, *IlAm. J. Psychiatry*, Apr. 1978, vol. 135, No. 4, pp. 472-475.

(56) References Cited

OTHER PUBLICATIONS

Rogers, S.J. et al.(Jan. 2008). "Evidence-Based Comprehensive Treatments for Early Autism," *J. Clin. Child. Adolesc. Psychol.* 37(1):8-38, thirty-eight pages.
Rolfe, P. (2000). "In Vivo Near-Infrared Spectroscopy," *Annual Review of Biomedical. Engineering* 2:715-754.
Rossignol, D.A. et al. (2008). "Evidence of Mitochondrial Dysfunction in Autism and Implications for Treatment," *American Journal of Biochemistry and Biotechnology* 4(2):208-217.
Schudel, P. et al. (1963). Uber die Chemie des Vitamins E. 5. Mitteilung. Die Synthese von rac. all-trans-.zeta..sub.1-und-.epsilon.-Tocopherol, *Helvetica Chimica Acta* 46(7):2517-2526, English summary on p. 2526.
Scott, J.W. et al. (1976). "Syntheses of (2R,4'R,8'R)-.alpha.-Tocopherol and (2 R,3'E,7'E)-.alpha.-Tocotrienol," *Helvetica Chimica Acta* 59:290-306, Nr. 34.
Shi, et al. "Hydrophobic Acceleration of Electron Transfer Processes", *Journal of Organic Chemistry*, 1996, vol. 61, pp. 4698-4702.
Shiraishi, M. et al. (Sep. 1989). "Quinones. 4. Novel Eicosanoid Antagonists: Synthesis and Pharmacological Evaluation," *Journal of Medicinal Chemistry* 32(9):2214-2221.
Siegel, D. et al. (1997). "The Reduction of a-Tocopherolquinone by Human NAD(P)H: Quinone Oxidoreductase: The Role of aTocopherolhydroquinone as a Cellular Antioxidant," *Molecular Pharmacology* 53:300-305.
Sigman, M. et al. (2004). "Early Detection of Core Deficits in Autism," *Mental Retardation and Developmental Disabilities Research Reviews*, vol. 10, pp. 221-233.
Silbert, L.S. et al. (Jun. 2, 1959). "Peroxides. VI. Preparation oft-Butyl Peresters and Diacyl Peroxides of Aliphatic Monobasic Acids," *Journal of the American Chemical Society* 81(10): 2364-2367.
Soll, et al. (Aug. 1-6, 1983). Inhibitor Binding and Displacement in Plastoquinone Depleted Chloroplasts, *Advances in Photosynthesis Research, Proceedings of the International Congress of Photsynthesis*, Brussels, Belgium IV.1:5-8.
Spoyalov, Andrei P. et al. "Endor and Eseem studies of Ion Radicals of Artificial Dimethoxy-or Halogen-1,4-benzoquionones with an Alkyl Side Chain of Differing Length," *J. Chem. Soc. Perkins Trans.*, 1992, pp. 1519-1524.
Staniek, K. et al. (Nov. 1, 2005). "The Protection of Bioenergetic Functions in Mitochondria by New Synthetic Chromanols," *Biochemical Pharmacology* 70(9):1361-1370.
Steghens, J.-P. et al. (2001). "Diaminonaphtalene, a New Highly Specific Reagent for HPLC-UV Measurement of Total and Free Malondialdehyde in Human Plasma or Serum," *Free Radical Biology & Medicine* 31(2):242-249.
STN Accession No. 1985:621368, last visited Jan. 23, 2007, 1 page.
STN Accession No. 1992:58878, last visited Jan. 23, 2007, 1 page.
STN Accession No. 1993;21870, last visited Jan. 23, 2007, 2 pags.
Strangman, G. et al. (Oct. 1, 2002). "Non-Invasive Neuroimaging Using Near-infrared Light," *Biological Psychiatry* 52(7):679-693.
Sue et al. "Mitochondria Respirtory Chain Diseases and Mutations in Nuclear DNA: A promising Start?" *Brain Pathalogy*, 2000, vol. 10, pp. 442-450.
Taivassalo, T. et al. (Feb. 2003). "The Spectrum of Exercise Tolerance in Mitochondrial Myopathies: A Study of 40 Patients," *Brain* 126(Pt2), pp. 413-423.
Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Annals of Neurology*, 51(1):38-44.
Thomas, A.D. et al. (Aug. 8, 1986). "Repetitive Diels-Alder Reactions for the Growth of Linear Polyacenequinoid Derivatives," *Journal of Organic Chemistry* 51(22):4160-4169.
Trumpower, B.L. (Jul. 15, 1990). "The Protonmotive Q Cycle. Energy Transduction by Coupling of Proton Translocation to Electron Transfer by Cytochrome bc.sub.1 Complex," *The Journal of Biological Chemistry* 265(20):11409-11412.
Ueda, K. et al. (Feb. 1997). "Evaluation of Changes in Hepatic Energy Metabolism during Exercise by Ketone Body Ration in Humans," *Journal of Cardiology* 29(2):95-102.
Urano, et al. (1983). "Synthesis of dl-a-Tocopherol and dl-a-Tocotrienol," *Chem. Pharm. Bull.* 31(12):4341-4345.
Van Beekvelt, M.C.P. et al. (Oct. 1999). "Quantivative Near-Infared Spectroscopy Discriminates Between Mitochondrial Myopathies and Normal Muscle," *Annals of Neurology* 46(4):667-670.
Vatassery, G. et al. (Apr. 5, 2004). "Iron Uncouples Oxidative Phosphorylation in Brain Mitochondria Isolated From Vitamin E-Deficient Rats," *Biochimica et Biophysica Acta* 1688(3):265-273.
Volkmar, F. et al. (2005, e-pub. Sep. 14, 2004). "Autism in Infancy and Early Childhood," *Annu. Rev. Psychol.* 56:315-336.
Walter, et al. "Three Classes of Ubiquinone Analogs Regulate the Mitochondrial Permeability Transition Pore through a Common Site," *The Journal of Biological Chemistry*, 2000, vol. 275, No. 38, pp. 29521-29527.
Weichet et al. "Collection of Czechoslovak Chemical Communications", (1966), vol. 31, No. 12, pp. 4598-4609.
Written Opinion dated Apr. 16, 2010, for PCT Patent Application No. PCT/US2010/25447, filed on Feb. 25, 2010, 5 pages.
Written Opinion dated Feb. 8, 2007, for PCT Patent Application No. PCT/US2006/036052 filed on Sep. 15, 2006, 11 pages.
Written Opinion of the International Searching Authority dated Nov. 12, 2009, for PCT Patent Application No. PCT/US2009/056254, filed on Sep. 8, 2009, 6 pages.
Written Opinion of the International Searching Authority dated Apr. 16, 2010, for PCT Patent Application No. PCT/US2010/25447, filed on Feb. 25, 2010, 5 pages.
Zheng, A. et al. (1999). "A Redox-Sensitive Resin Linker for the Solid Phase Synthesis of C-Terminal Modified Peptides," *Journal of Organic Chemistry* 64:156-161.
Zwaiyed, F.R. et al. (2003). "Vitamin E and its Derivative Antihypoxic Effectivity in Rats Under Modeling of Hypoxic Conditions of Different Origin," *Ukrainskii Biokhimicheskii Zhurnal* 75(2):67-71.
1957:81330 CAPLUS, Weichet et al., "Studies in the vitamin K and E series, III, Analogs of a-tocopherol with unbranched sidechains", 1 page.
202843-61-6 Registry, Mar. 19, 1998, 2,5-Cyclohexadiene-1,4-dione, 2,3,5-trimethyl-6-[(2E)-3-methyl-2-nonen-1-yl], 1 page.
82925-41-5 Registry, Nov. 16, 1984, 1,4-Benzenediol, 2,3,5-trimethyl-6-(3-methyl-2-nonadeceri-1-yl), 1 page.
Anonymous (1976), "028 CGI Clinical Global Impressions," in Early Clinical Drug Evaluation Unit (ECDEU) Assessment Manual for Psychopharmacology, U.S. Department of Health, Education, and Welfare, pp. 217-222.
Anonymous (2006), "Mitochondrial Dysfunction Contribution to Bipolar Disorder Confirmed Using Model Mice," Press Release from Riken Brain Science Institute located at http://web.archive.org/web/2012030316199/htto://www.riken.ip/enon/r-world/infor/pressrelease/press/2006/060418/index.html, last visited Feb. 10, 2015, 5 pages.
Anonymous, ICD-10 Version:2015, "Other specified degenerative diseases of nervous system" located at http://apps.who.int/classifications/icd10/browse/2015/en#/G31.8, the site was last visited on May 12, 2016, 1 page.
Anonymous. (2011). "Mitochondrial Myopathy," located at http://www.ninds.nih.gov/disorders/mitochondrial_myopathy/mitochondrial_myopathy.html, last visited Feb. 10, 2015, 2 pages.
Bentinger, M. et al. (May 23, 2008). "Polyisoprenoid Epoxides Stimulate the Biosynthesis of Coenzyme Q and Inhibit Cholesterol Synthesis," The Journal of Biological Chemistry, vol. 283, No. 21, pp. 14645-14653.
Bentinger, M. et al. (2008). "Stimulation of Coenzyme Q Synthesis," BioFactors 32, pp. 99-111.
Bernas T. et al. (2002). "Mitochondrial and Nonmitochondrial Reduction of MTT: Interaction of MTT With TMRE, JC-1, and NAO Mitochondrial Fluorescent Probes," Cytometry 47:236-242.
Berridge M. et al. (2005). "Tetrazolium dyes as tools in cell biology: New insights into their cellular reduction," Biotechnology Annual Review 11:127-152.

(56) References Cited

OTHER PUBLICATIONS

Bertalan L. et al. (2000). "Recovery of fatty oil from the Transylvanian black current by means of supercritical and conventional extraction," Olaf, szappn Kozmetika 49(Kulonszam), pp. 40-45.
Bertamini, M. et al. (2002). "Mitochondrial Oxidative Metabolism in Motor Neuron Degeneration (mnd) Mouse Central Nervous System," European Journal of Neuroscience 16(12):2291-2296.
Bridgelius-Flohe, R. et al. (Jul. 1999). "Vitamin E: Function and Metabolism," The FASEB Journal, vol. 13, No. 10, pp. 1145-1155.
Butterfield, D.A. et al. (2002). "Vitamin E and Neurodegenerative Disorders Associated with Oxidative Stress," Nutritional Neuroscience 5(4):229-239.
Catlin Joseph C et al: "New Hydroquinones, Apparent Inhibitors of Coenzyme Q Enzyme Systems", Journal of the American Chemical Society, Jun. 19, 1968 (Jun. 19, 1968), pp. 3572-3574, XP55065560, Retrieved from the Internet: LIRL:httgil_pubs.acs.oratdoilpal 0.1021lia01015a054 [retrieved on Jun. 6, 2013].
Choi, D.W. (Oct. 1988). "Glutamate Neurotoxicity and Diseases of the Nervous System," Neuron. 1(8):623-634.
Chow, C.K. et al. (Sep. 1967). "The Metabolism of C14-a-Tocopheryl Quinone and C14-a-Tocopheryl Hydroquinone," Lipids 2(5):390-396.
Christen et al. (Apr. 1997). "γ-Tocopherol Traps Mutagenic Electrophiles Such as NOX and Complements α-Tocopherol: Physiological Implications," Proc. Natl. Acad. Sci. USA 94(7):3217-3222.
Cichewicz, R.H. et al. (2004, e-pub. Oct. 23, 2004). "Redox Inactivation of Human 15-Liopsygenase by Marine-Derived Meroditerpenes and Synthetic Chromanes: Archetypes for a Unique Class of Selective and Recyclable Inhibitors," Journal of the American Chemical Society 126(45):14910-14920.
Fahey et al., (2004). "The "Prochaska" Microtiter Plate Bioassay for Inducers of NQO1," Chapter 14 in Methods in Enzymology, Quinones and Quinone Enzymes, Part B, Sies H, ed., Elsevier Academic Press, San Diego, CA, pp. 243-258.
Fryer, M.J. (1998). "Vitamin E Status and Neurodegenerative Disease," Nutritional Neuroscience 1(5):327-351.
Fukuzawa, K. et al. (Jul. 1982). "Antioxidant Activities of Tocopherols on Fe2+-ascorbate-Induced Lipid Peroxidation in Lecithin Liposomes," Lipids 17(7):511-513.
Gille, L. et al. (2010); "Tocopheryl Quinones and Mitochondria," Mol. Nutr. Food Res. 54:1-15.
Grau, A. et al. (1998); "Dissimilar Protection of Tocopherol Isomers Against Membrane Hydrolysis by Phospholipase A2," Chemistry and Physics of Lipids 91:109-118.
Gubskii et al. (2008). "Antioxidant and Membranotropic Effects of Monochromanes and Trimethylphenol Derivatives in Vitro," Ukrains'kii Biokhimichnii Zhumal 80(6):79-85, Chemical Abstract Only, CAPLUS Abstract No. 2009:267923.
Haas et al. (May 2008); "The In-Depth Evaluation of Suspected Mitochondrial Disease: The Mitochondrial Medicine Society's Committee on Diagnosis," Mol. Genet. Metab. 94(1):1637, 32 pages.
Han, J. (2006); "Advances in Characterization of Pharmaceutical Hydrates," Trends in Bio/Pharmaceutical Industry 3:25-29.
Hawkins, R.D. et al. (1993). "Learning to Modulate Transmitter Release: Themes and Variations in Synaptic Plasticity," Annual Review of Neuroscience 16:625-665.
Hendlin, D. et al. (Apr. 1960) "The Activity of Coenzyme Qlo and Its Analogues in the Succinoxidase System of Electron Transport Particles," Journal of Biological Chemistry, 235(4):1187-1191.
Hodgkiss et al. (May 1989). "The Effect of α-tocopherol and α-tocopheryl quinone on the Radiosensitivity of Thiol-Depleted Mammalian Cells," International Journal of Radiation Oncology, Biology, Physics 16(5), pp. 1297-1300.
Jaiswal, A.K. (2000). "Characterization and Partial Purification of Microsomal NAD(P)H:Quinone Oxidoreductases," Archives of Biochemistry and Biophysics 375(1):62-68.
Jiang, Q. et al. (Oct. 10, 2000). γ-Tocopherol and its Major Metabolite, in Contrast to α-Tocopherol, Inhibit Cyclooxygenase Activity in Macrophages and Epithelial Cells, Proceedings of the National Academy of Sciences 97(21):11494-11499.
Jones, J.W. et al. (1977). "10% Soybean Oil Emulsion As a Myocardial Energy Substrate After Ischemic Arrest," Surgical Forum 28:284-285.
Jung, M E et al: "First Enantioselective Total Synthesis of the Endogenous Natriuretic Agent LLU-Alpha", Tetrahedron Letters, Elsevier, Amsterdam, NL, vol. 40, No. 25, Aug. 27, 1999 (Aug. 27, 1999), pp. 6339-6342, XP004173857, ISSN: 0040-4039, DOI: 10.1016/S00404039(99)01204-6.
Jung, M.Y. et al. (Sep. 1, 1990). "Effects of α-, γ-, and δ-Tocopherols on Oxidative Stability of Soybean Oil," Journal of Food Science 55(5), pp. 1464-1465.
Kamat, J.P. et al. (1995). "Tocotrienols from Palm Oil as Potent Inhibitors of Lipid Preoxidation and Protein Oxidation in Rat Brain Mitochondria," Neurosci. Lett. 195, pp. 179-182.
Kanno, T. et al. (1996). "Inhibition of Neutrophil-Superoxide Generation by α-Tocopherol and Coenzyme Q," Free Radical Research 24(4), pp. 281-289.
Karry, R. et al. (2004). "Mitochondria! Complex I Subunits Expression Is Altered in Schizophrenia: A Postmortem Study," Biological Psychiatry 55(7), pp. 676-684.
Keeney et al. (May 10, 2006). "Parkinson's Disease Brain Mitochondrial Complex I Has Oxidatively Damaged Subunits and Is Functionally Impaired and Misassembled," The Journal of Neuroscience 26(19), pp. 5256-5264.
Khanna, S. et al. (2005, e-published Sep. 15, 2005). "Neuroprotective Properties of the Natural Vitamin E α-Tocotrienol," Stroke 36:e144-e152.
Kobayashi, M.S. et al. (2000). "Antioxidants and Herbal Extracts Protech HT-4 Neuronal Cells Against Glutamate-Induced Cytotoxicity," Free Radical Research 32(2), pp. 115-124.
Kovalenko, V.N. et al. (1979); "Vitamin E Activity of Vitamin E Derivatives in Experimental Encephalomalacia in Chicks," Ukrainskii Biokhimicheskii Zhumal 51(6):665-668, Chemical Abstract Only, CAPLUS Abstract No. 1980:74772, 1 page.
Kunitsa et al. (Nov. 1993); "Effects of Tocopherol and its Analogs on in vivo Lipid Peroxidation and Electron Transport in Rat Liver Mitochondria," Biochemistry (Moscow) an International Journal 58(11), pp. 1256-1259.
Kwong, J.Q. et al. (2006). "The Role of Mitochondria in Inherited Neurodegenerative Diseases," Journal of Neurochemistry 97, pp. 1659-1675.
Makovetskii, V.P. et al. (1987). "Synthesis, Properties, and Detoxication Activity of a-tocopherol Analogs and Derivatives," Khimiko-Farmatsevticheskii Zhumal21(12):1441-1446, Chemical Abstract Only, CAPLUS Abstract No. 1988:142850, 2 pages.
Moore, A.N.J. et al. (1997). "a-Tocopheryl Quinone is Converted into Vitamin E in Man," Free Radical Biology & Medicine 22(5):931-934.
Mukai et al, "Stopped-flow kinetic study of vitamin E regeneration reaction with biological hydroquinones (reduced forms of ubiquinone, vitamin K, and tocopherolquinone) in solution", J Biol Chem, Nov. 5, 1992, vol. 267, No. 31, pp. 22277-22281.
Ogawa et al. (Jul. 2008). Free Radical Research, vol. 42(7), pp. 674-687.
Olichon, A. et al. (2006, e-pub. Apr. 20, 2006). "Mitochondrial Dynamics and Disease, OPA1," Biochimica et Biophysica Acta 1763:500-509.
Park, L.C.H. et al. (2000). "Metabolic Impairment Elicits Brain Cell Type-Selective Changes in Oxidative Stress and Cell Death in Culture," Journal of Neurochemistry 74(1):114-124.
Prochaska H.J. et al. (1988). "Direct measurement of NAD(P)H:quinone reductase from cells cultured in microtiter wells: a screening assay for anticarcinogenic enzyme inducers," Anal. Biochem. 169, pp. 328-336.
Ricciarelli, R. et al. (1998). "α-Tocopherol Specifically Inactivates Cellular Protein Kinase C α by Changing Its Phosphorylation State," Biochem. J. 334, pp. 243-249.
Sen, C.K. et al. (2007). "Tocotrienols in Health and Disease: The Other Half of the Natural Vitamin E Family," Mol. Aspects Med. 28(5-6):692-728.
Sen, C.K. et al. (Apr. 28, 2000); "Molecular Basis of Vitamin E Action. Tocotrienol Potently Inhibits Glutamate-Induced pp60c-Src

(56) References Cited

OTHER PUBLICATIONS

Kinase Activation and Death of HT4 Neuronal Cells," The Journal of Biological Chemistry 275(17):13049-13055.
Tabrizi, S.J. et al. (Jul. 1998). "Primary and Secondary Deficiencies of the Mitochondrial Respiratory Chain," The Neurologist 4(4):169-179.
Theriault, A. et al. (Jul. 1999). "Tocotrienol: A Review of Its Therapeutic Potential," Clinical Biochemistry 32(5):309-319.
Timochko, M.F. et al. (1998). "Metabolic Aspects of Oxygen Homeostasis Formation Under Extreme Conditions," with English translation of paragraph 5 on p. 7, L'vov, located at <http://posrednik.ru/tren/tim_sv.htm>, last visited on Sep. 29, 2008, 52 pages.
Van Haaften, R.I.M. et al. (Mar. 15, 2001). "No Reduction of α-Tocopherol Quinone by Glutathione in Rat Liver Microsomes," Biochemical Pharmacology 61(6):715-719.
Wang, J-F. (Dec. 2007). "Defects of Mitochondrial Electron Transport Chain in Bipolar Disorder: Implications for Mood-Stabilizxing Treatment," The Canadian Journal of Psychiatry 52(12):753-762.
Wechter, W.J. et al. (Jun. 1996). "A New Endogenous Natriuretic Factor: LLU-α," Proc. Natl. Acad. Sci. USA 93:6002-6007.
Weichet J. et al. "New Substituted Benzohydroquinones", Chemical Abstracts Service, Columbus, Ohio, US; Database CA, XP002698443, retrieved from STN Database accession No. 1968:95542; 1 page.
Yamauchi, R. et al. (1990). "Reaction of 5-Tocopherol with an Alkylperoxyl Radical," Agricultural and Biological Chemistry 54(11):2993-2999.
Yamauchi, R. et al. (1990). "Reaction Products of y-Tochopherol with an Alkylperoxyl Radical in Benzene," Agricultural and Biological Chemistry 54(10):2703-2709.
Yamauchi, R. et al. (1996). "Oxidation of a-Tocopherol during the Peroxidation of Dilinoleoylphosphatidylcholine in Liposomes," Bioscience, Biotechnology, and Biochemistry 60(4):616-620.
Yang, S.-G. et al. (Dec. 2010, e-pub. Oct. 7, 2010). "Alpha-Tocopherol Quinone Inhibits Beta-Amyloid Aggregation and Cytotoxicity, Disaggregates Preformed Fibrils and Decreases the Production of Reactive Oxygen Species, NO and Inflammatory Cytokines," Neurochemistry International 57(8):914-922.

TREATMENT OF PERVASIVE DEVELOPMENTAL DISORDERS WITH REDOX-ACTIVE THERAPEUTICS

CROSS-REFERENCE TO RELATED APPLICATIONS

This application claims priority benefit of U.S. Provisional Patent Application No. 61/191,696 filed Sep. 10, 2008. The content of that application is hereby incorporated by reference herein in its entirety.

FIELD OF THE INVENTION

The application discloses redox-active compositions and methods useful for treatment, prevention, or suppression of diseases, developmental delays and symptoms of pervasive developmental disorders including autistic spectrum disorders and/or attention deficit/hyperactivity disorder.

BACKGROUND OF THE INVENTION

Pervasive developmental disorder (PDD) is a category of neurological disorders characterized by severe and pervasive impairment in several areas of development, including social interaction and communications skills. The five disorders under PDD are autistic disorder (autism), Asperger's syndrome, childhood disintegrative disorder (CDD), Rett's disorder, and PDD-not otherwise specified (PDD-NOS). Specific diagnostic criteria for each of these disorders can be found in the Diagnostic & Statistical Manual of Mental Disorders (DSM-IV-TR) as distributed by the American Psychiatric Association (APA). Autistic spectrum disorder (ASD) is an umbrella term that is used to represent a broad heterogeneous disorder by collectively grouping autistic disorder, Asperger's syndrome and PDD-NOS.

Autism, the most common of the pervasive developmental disorders, affects an estimated 1 in approximately 150 births. Estimates of the prevalence of ASD are in the range of 6.5 to 6.6 per 1000 based on Autism and Developmental Disabilities Monitoring Network Surveillance (Year 2002). Indeed, as of 2003-2004, as many as 1.5 million Americans are believed to have some form of autism. Autism is a childhood encephalopathy characterized by deficiencies in social interaction and communication and by repetitive and stereotyped behaviors. Based on statistics from the U.S. Department of Education and other governmental agencies, autism is growing at a rate of 10-17 percent per year. At these rates, the Autism Society of America (ASA) estimates that the prevalence of autism could easily reach 4 million Americans in the next decade.

Of the other four PDD forms, Asperger's syndrome is closest to autism in signs and likely causes; Rett's disorder and childhood disintegrative disorder share several signs with autism, but may have unrelated causes; PDD-not otherwise specified (PDD-NOS) is diagnosed when the criteria are not met for a more specific disorder (Lord C, et al. "Autism spectrum disorders" *Neuron* (2000) 28 (2): 355-63).

Autism is a complex serious developmental disability that interferes with, among other things, the normal development of the brain in the areas of social interaction and communication skills, and which causes severely restricted interests and repetitive behavior. Typically, autistic children and adults have difficulties in verbal and non-verbal communication, social interactions, and leisure or play activities. Autism can include language disorders with impaired understanding, echolalia, pronominal reversal (such as using "you" instead of "I" or "me" when referring to one's self), rituals and compulsive phenomena, and uneven intellectual development with mental retardation. Autistic children are also at increased risk of developing seizure disorders, especially during their teen years. Autism typically appears during the first three years of life and is the result of a neurological disorder that affects the functioning of the brain.

The overall incidence of autism is, for the most part, globally consistent. Indeed, autism knows no racial, ethnic, or social boundaries, and family income, lifestyle, and educational levels do not affect the chance of autism's occurrence. However, it has been found to be four times more prevalent in boys than girls. On the other hand, Rett's disorder is more prevalent in girls than boys.

Since being first described by Dr. Leo Kanner in 1943, the understanding of autism has grown tremendously. Although autism is defined by a certain set of behaviors, it is a spectrum disorder in that its symptoms and characteristics can be present in a wide variety of combinations, from mild to severe. Therefore, autistic children and adults can exhibit any combination of the behaviors in any degree of severity. Two individuals, both with the same diagnosis, may have varying skills and display very different actions. Those only mildly affected may exhibit slight delays in language or communication and may face greater challenges in social interactions. For example, one may have difficulty initiating and/or maintaining a conversation. Communication by autistic children or adults is often displayed as talking at others (for example, a monologue on a favorite subject that continues despite attempts by others to interject comments).

Autism seems to cause those affected by it to process and respond to information in unique ways. In some individuals with PDD including autism, aggressive and/or self-injurious behavior may exist. The following traits, as identified by the ASA, may also be present in persons with autism: insistence on sameness or resistance to change; difficulty in expressing needs (i.e. uses gestures or pointing instead of words); repeating words or phrases in place of normal, responsive language; laughing, crying, or showing distress for reasons not apparent to others; preferring to be alone or an aloof manner; tantrums; difficulty in mixing with others; not wanting to cuddle or be cuddled; little or no eye contact; unresponsive to normal teaching methods; sustained, odd play; spinning objects; inappropriate attachments to objects; apparent over-sensitivity or under-sensitivity to pain; no real fears of danger; marked physical over-activity or extreme under-activity; uneven gross/fine motor skills; and/or non-responsiveness to verbal cues (i.e. acts as if deaf although hearing tests in normal range).

Symptoms as in attention deficit hyperactivity disorder (ADHD) are frequent among individuals with pervasive developmental disorders (PDD). Children meeting diagnostic criteria for a pervasive developmental disorder (PDD) display symptoms and impairment related to attention deficit hyperactivity disorder (ADHD) sufficient to warrant a diagnosis of ADHD (Goldstein S, et al "The Comorbidity of Pervasive Developmental Disorder and Attention Deficit Hyperactivity Disorder: Results of a Retrospective Chart Review" *Journal of Autism and Developmental Disorders*, (2004) 34 (3):329-339). Hattori J. et al "Are Pervasive Developmental Disorders and Attention Deficit/Hyperactivity Disorder Distinct Disorders?" studied the relationship between patients with attention deficit/hyperactivity disorder (ADHD) and those with pervasive developmental disorders (PDD), using the High-Functioning Autism Spectrum Screening Questionnaire (ASSQ) and ADHD Rating Scale-IV. The patients with strictly diagnosed ADHD had many PDD-related symptoms, and the patients with PDD had many ADHD-related symptoms. It therefore seems difficult to make a distinction between ADHD and PDD by using the present diagnostic criteria in the DSM-IV.

People with autism have social impairments that appear early in childhood and continue through adulthood. Autistic infants show less attention to social stimuli, smile and look at others less often, and respond less to their own name. Autistic toddlers have more striking social deviance: for example, they have less eye contact and anticipatory postures and are more likely to communicate by manipulating another person's hand (Volkmar F, et al "Autism in infancy and early childhood," *Anna Rev Psychol* (2005) 56: 315-36.) Three- to five-year-old autistic children are less likely to exhibit social understanding, approach others spontaneously, imitate and respond to emotions, communicate nonverbally, and take turns with others. However, they do form attachments to their primary caregivers. (Sigman M, et al. "Early detection of core deficits in autism" *Ment Retard Dev Disabil Res Rev*. (2004) 10 (4); 221-33). They display moderately less attachment security than usual, although this feature disappears in children with higher mental development or less severe autism spectrum disorders. Older children and adults with ASD perform worse on tests of face and emotion recognition (Sigman M. et al, see supra). Contrary to common belief, autistic children do not prefer to be alone. Making and maintaining friendships often proves to be difficult for those with autism. For them, the quality of friendships, not the number of friends, predicts how lonely they are.

Unlike those with autism, people with Asperger's syndrome are not usually withdrawn around others; they approach others, even if awkwardly, for example by engaging in a one-sided, long-winded speech about a favorite topic while being oblivious to the listener's feelings or reactions, such as signs of boredom or haste to leave.

About a third to a half of individuals with autism does not develop enough natural speech to meet their daily communication needs; (Noens I, et al, "The ComFor: an instrument for the indication of augmentative communication in people with autism and intellectual disability". *J Intellect Disabil Res* (2006) 50 (9): 621-32.) Differences in communication may be present from the first year of life, and may include delayed onset of babbling, unusual gestures, diminished responsiveness, and the desynchronization of vocal patterns with the caregiver. In the second and third years, autistic children have less frequent and less diverse babbling, consonants, words, and word combinations; their gestures are less often integrated with words. Autistic children are less likely to make requests or share experiences, and are more likely to simply repeat others' words or reverse pronouns.

For individuals with autism, sensory integration problems are common. In particular, their senses may be either over- or under-active. The fuzz of a kiwi may actually be experienced as painful; a sweet, fruity smell may cause a gagging reflex. Some children or adults with autism are particularly sensitive to sound, so that even the most ordinary daily noises are painful.

Although there is no single known cause for autism, it is generally accepted that it is caused by abnormalities in brain structure or function. The shape and structure of the brain in autistic versus non-autistic children show differences when brain scans are viewed. Currently the links between heredity, genetics and medical problems are being investigated by researchers, as well as a number of other theories. The theory of a genetic basis of the disorder is supported by the fact that, in many families, there appears to be a pattern of autism or related disabilities. While no one gene has been identified as causing autism, researchers are searching for irregular segments of genetic code that autistic children may have inherited. While researchers have not yet identified a single trigger that causes autism to develop, it also appears that some children are born with a susceptibility to autism.

Other researchers are investigating the possibility that under certain conditions, a cluster of unstable genes may interfere with brain development resulting in autism. Still other researchers are investigating problems during pregnancy or delivery as well as environmental factors such as viral infections, metabolic imbalances, and exposure to environmental chemicals. Yet other researchers are investigating the link between autism and chemical toxicity, in particular with the mercury-containing vaccine preservative thimerosal.

Some cases of autism have been associated with several different organic conditions, including bioenergetic metabolism deficiency suggested by the detection of high lactate levels in some patients (Coleman M. et al, Autism and Lactic Acidosis, *J. Autism. Dev Discord.*, (1985) 15: 1-8; Laszlo et al Serum serotonin, lactate and pyruvate levels in infantile autistic children, *Clin. Chim. Acta* (1994) 229:205-207; and Chugani et al., Evidence of altered energy metabolism in autistic children, *Progr. Neuropsychopharmacol Biol Psychiat.*, (1999) 23:635-641) and by nuclear magnetic resonance imagining as well as positron emission tomography scanning which documented abnormalities in brain metabolism. Although the mechanism of hyperlactacidemia remains unknown, a likely possibility involves mitochondrial oxidative phosphorylation dysfunction in neuronal cells. A small subset of autistic patients diagnosed with deficiencies in complex I or III of the respiratory chain have been reported in the literature (see Oliveira, G., *Developmental Medicine & Child Neurology* (2005) 47 185-189; and Filipek, Pa. et al., *Journal of Autism and Developmental Disorders* (2004) 34:615-623.) However, in many of the cases of autism where there is some evidence of mitochondrial dysfunction, there is an absence of the classic features associated with mitochondrial disease, such as mitochondrial pathology in muscle biopsy (see Rossignol, D. A. et al., *Am J. Biochem. & Biotech*, 4 (2) 208-217).

The main goals of treatment are to lessen associated deficits and family distress, and to increase quality of life and functional independence. No single treatment is best and treatment is typically tailored to the child's needs. Intensive, sustained special education programs and behavior therapy early in life can help children acquire self-care, social, and job skills, (Myers S M, et al. "Management of children with autism spectrum disorders" *Pediatrics* (2007) 120 (5): 1162-82) and Angley M, et al. "Children and autism—part 1—recognition and pharmacological management" *Aus.t Fain. Physician* (2007) 36 (9): 741-4) and often improve functioning and decrease symptom severity and maladaptive behaviors; (Rogers S J, et al., "Evidence-based comprehensive treatments for early autism" *J Clin. Child Adolesc. Psycho*. (2008) 37 (1): 8-38)

Medications have not been proven to correct deficits of ASDs and are not the primary treatment. They are used to treat problems associated with autism disorders, such as associated maladaptive behaviors or psychiatric comorbidities that may interfere with educational progress, socialization, health or safety and quality of life. More than half of U.S. children diagnosed with autistic disorders are prescribed psychoactive drugs or anticonvulsants, with the most common drug classes being antidepressants, stimulants, and antipsychotics. (Oswald D P, et al. "Medication Use Among Children with Autism Spectrum Disorders". *J. Child Adolesc Psychopharmacol* (2007) 17 (3): 348-55.) Aside from antipsychotics, there is scant reliable research about the effectiveness or safety of drug treatments for children, adolescents or adults with ASD. A person with ASD may respond atypically to medications, the medications can have adverse effects, and no known medication relieves autism's core symptoms of social and communication impairments. Alternative nutritional therapies for autistic children may include Idebenone and CoQ10, because of their superior antioxidant properties, but no studies have been performed to prove their efficacy.

US Patent Publication 2005/0203066 discloses compounds, compositions and methods for treatment of developmental delay in cognitive, motor, language, executive function or social skills with a pyrimidine nucleotide precursor, but it does not disclose any compounds, compositions or methods of treatment with compounds of the present invention.

Attention deficit hyperactivity disorder (ADHD) also referred to as ADD is a biological, brain based condition that is characterized by poor attention and distractibility and/or hyperactive and impulsive behaviors. It is one of the most common mental disorders that develop in children. Symptoms may continue into adolescence and adulthood. If left untreated, ADHD can lead to poor school/work performance, poor social relationships and a general feeling of low self esteem. The most prevalent symptoms of ADHD are inattention and distractibility and/or hyperactive and impulsive behaviors. Difficulties with concentration, mental focus, and inhibition of impulses and behaviors are chronic and pervasive and impair an individual's daily functioning across various settings—home, school or work, in relationships, etc. ADD or attention deficit disorder is a general term frequently used to describe individuals that have attention deficit hyperactivity disorder (ADHD) without the hyperactive and impulsive behaviors. The terms are often used interchangeably for both those who do and those who do not have symptoms of hyperactivity and impulsiveness.

Thus, there is an unmet need for improved methods of treating patients with pervasive developmental disorders, particularly with autism and/or attention deficit/hyperactivity disorder (ADHD).

SUMMARY OF THE INVENTION

The present invention provides methods and redox-active compositions that can reduce the symptoms of autism in a human patient. Briefly, the methods and compositions comprise administering a physiologically effective amount of one or both of in sufficient quantities to reduce the effects of the autism. When administered to human patients suffering from autism, without restriction on the normal diet of the patients, the compositions and methods reduce or improve one or more symptoms of autism, such as increased eye contact, better enunciation and use of pronouns, less fatigue, singing a song for the first time with the melody and words together and the entire song understandable, playing with age appropriate friends for the first time, fewer tantrums, better sleep patterns, improved politeness and coordination, being more loving, acknowledging another individual's emotion, and increased voice and word association. The redox-active compounds of the present invention are superior because they show protective effect not only on cells of autistic patients that have a mitochondrial dysfunction but also on cells of patients that do not show any impairment of mitochondrial energy metabolism.

In one aspect, the invention embraces a composition for reducing the symptoms associated with, or for treating or suppressing pervasive developmental disorder (PDD), including autistic disorder, Asperger's syndrome, childhood disintegrative disorder (CDD), Rett's disorder, and PDD-Not Otherwise Specified (PDD-NOS) or attention deficit/hyperactivity disorder (ADHD) in a patient in need of such treatment comprising one or more compounds of Formula I, Formula II, Formula III, Formula IV, Formula V, Formula VI or mixtures thereof,

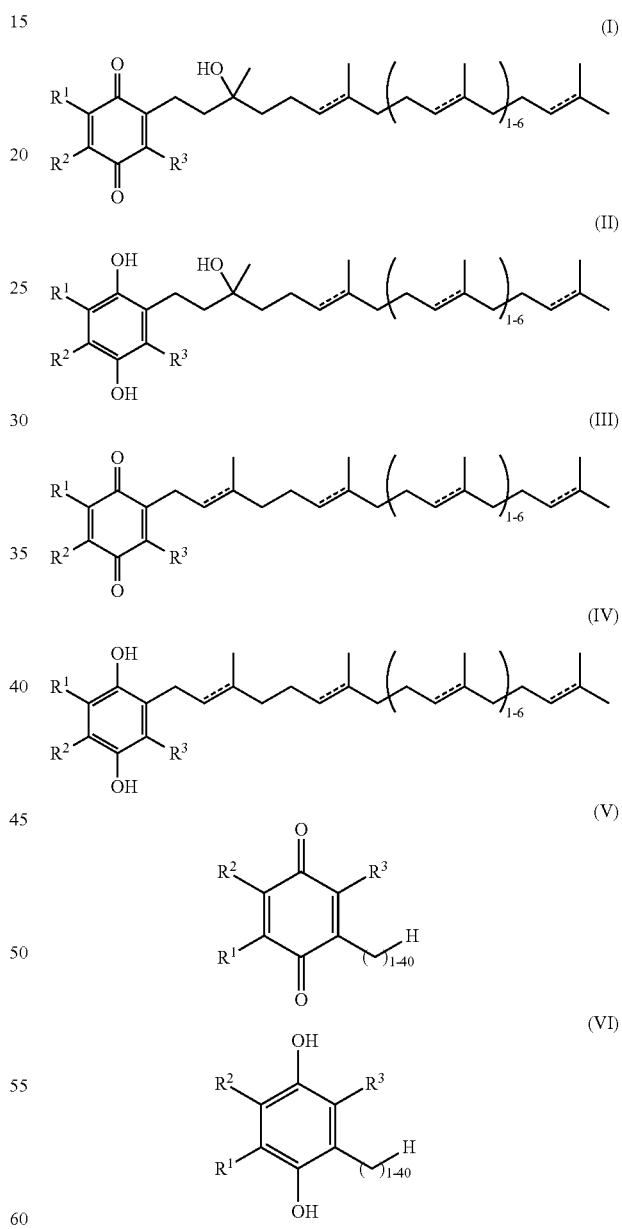

wherein,
the bonds indicated with a dashed line can independently be single or double;
$R^1$, $R^2$, and $R^3$ are independently selected from H, ($C_1$-$C_6$) alkyl, ($C_1$-$C_6$)haloalkyl, ($C_1$-$C_6$)alkoxy, halogen and CN;

and all salts, stereoisomers, mixtures of stereoisomers, pro-drugs, metabolites, solvates and hydrates thereof. In another embodiment, the bonds indicated with a dashed line are all single bonds. In another embodiment, the bonds indicated with a dashed line are all double bonds.

In one embodiment, $R^1$, $R^2$, and $R^3$ are independently selected from $(C_1-C_4)$alkyl, and in a particular example $R^1$, $R^2$, and $R^3$ are methyl. In another embodiment, at least one of $R^1$, $R^2$, and $R^3$ is not methyl. In another embodiment, $R^1$ and $R^2$ are independently selected from $(C_1-C_4)$alkoxy, and $R^3$ is $(C_1-C_4)$alkyl. In another embodiment, $R^1$ and $R^2$ are methoxy, and $R^3$ is methyl.

In one embodiment, the invention embraces a composition for reducing the symptoms associated with, or for treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment comprising one or more compounds of Formula Ia, Formula IIa, Formula IIIa, Formula IVa, Formula Va, Formula VIa, or mixtures thereof,

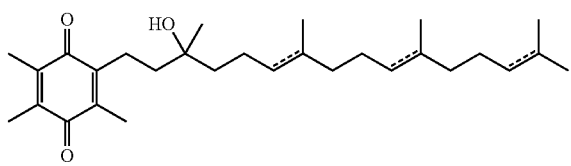
(Ia)

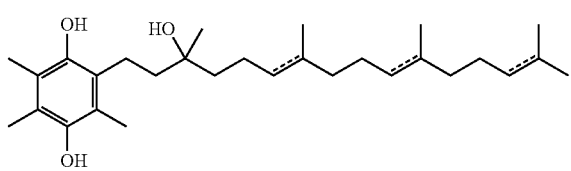
(IIa)

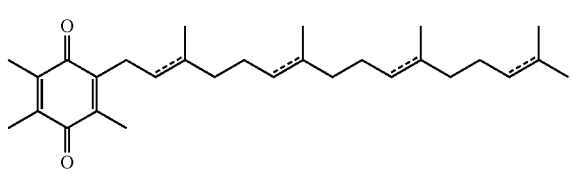
(IIIa)

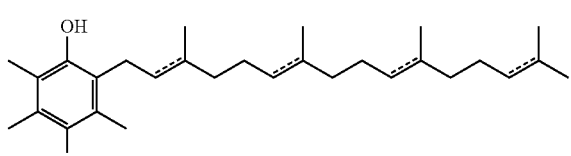
(IVa)

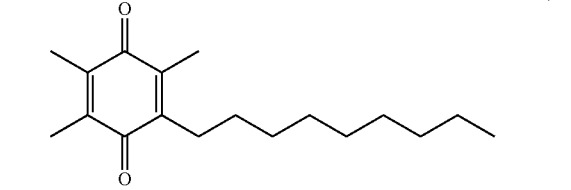
(Va)

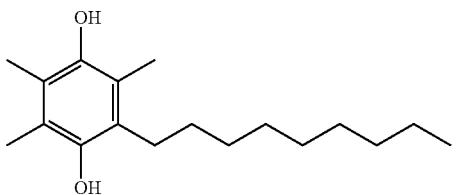
(VIa)

and all salts, stereoisomers, mixtures of stereoisomers, pro-drugs, metabolites, solvates and hydrates thereof. In another embodiment, the bonds indicated with a dashed line are all single bonds. In another embodiment, the bonds indicated with a dashed line are all double bonds.

In another aspect, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of one or more compounds of Formula I, Formula II, Formula III, Formula IV, Formula V, Formula VI, or mixtures thereof,

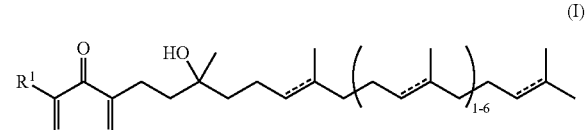
(I)

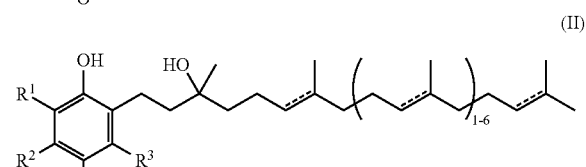
(II)

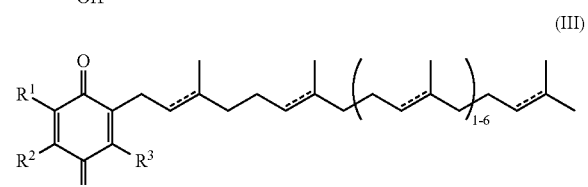
(III)

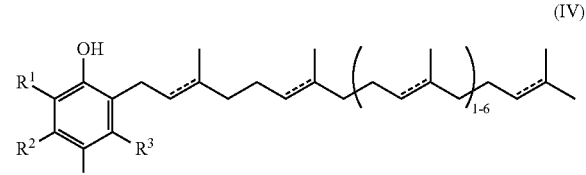
(IV)

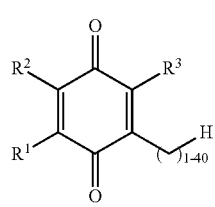
(V)

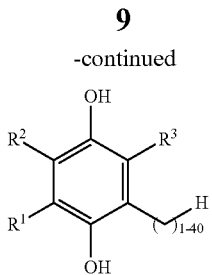

(VI)

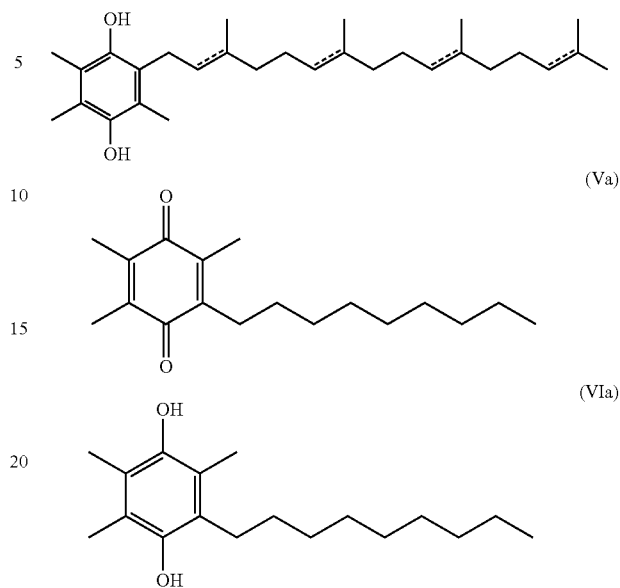

wherein,
the bonds indicated with a dashed line can independently be single or double;
$R^1$, $R^2$, and $R^3$ are independently selected from H, $(C_1\text{-}C_6)$ alkyl, $(C_1\text{-}C_6)$haloalkyl, $(C_1\text{-}C_6)$alkoxy, halogen and CN;
and all salts, stereoisomers, mixtures of stereoisomers, prodrugs, metabolites, solvates and hydrates thereof. In another embodiment, the bonds indicated with a dashed line are all single bonds. In another embodiment, the bonds indicated with a dashed line are all double bonds.

In one embodiment, $R^1$, $R^2$, and $R^3$ are independently selected from $(C_1\text{-}C_4)$alkyl, and in a particular example $R^1$, $R^2$, and $R^3$ are methyl. In another embodiment, at least one of $R^1$, $R^2$, and $R^3$ is not methyl. In another embodiment, $R^1$ and $R^2$ are independently selected from $(C_1\text{-}C_4)$alkoxy, and $R^3$ is $(C_1\text{-}C_4)$alkyl. In another embodiment, $R^1$ and $R^2$ are rnethoxy, and $R^3$ is methyl.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of one or more compounds of Formula Ia, Formula IIa, Formula IIIa, Formula IVa, Formula Va, Formula VIa, or mixtures thereof, and all salts, stereoisomers, mixtures of stereoisomers, prodrugs, metabolites, solvates and hydrates thereof. In another embodiment, the bonds indicated with a dashed line are all single bonds. In another embodiment, the bonds indicated with a dashed line are all double bonds.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of one or more compounds of Formula Id, Formula IId or mixtures thereof,

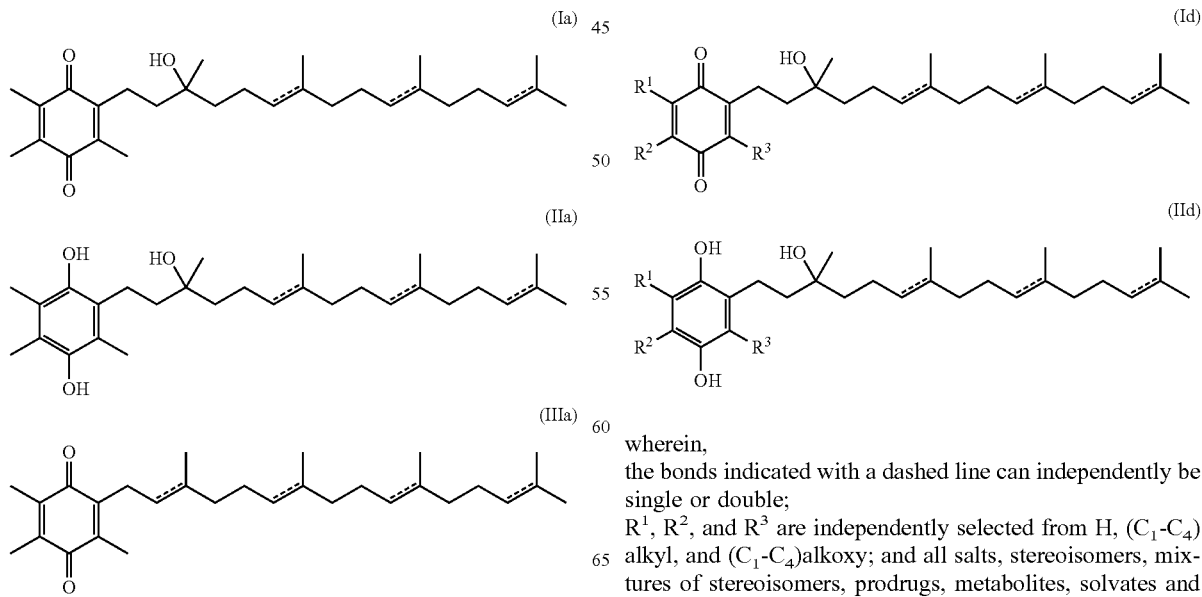

wherein,
the bonds indicated with a dashed line can independently be single or double;
$R^1$, $R^2$, and $R^3$ are independently selected from H, $(C_1\text{-}C_4)$ alkyl, and $(C_1\text{-}C_4)$alkoxy; and all salts, stereoisomers, mixtures of stereoisomers, prodrugs, metabolites, solvates and hydrates thereof. In another embodiment, the bonds indicated with a dashed line are all single bonds. In another embodiment, the bonds indicated with a dashed line are all double bonds.

In one embodiment, $R^1$, $R^2$, and $R^3$ are independently selected from $(C_1-C_4)$alkyl, and in a particular example $R^1$, $R^2$, and $R^3$ are methyl. In another embodiment, at least one of $R^1$, $R^2$, and $R^3$ is not methyl. In another embodiment, $R^1$ and $R^2$ are independently selected from $(C_1-C_4)$alkoxy, and $R^3$ is $(C_1-C_4)$alkyl. In another embodiment, $R^1$ and $R^2$ are methoxy, and $R^3$ is methyl.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of a compound of Formula Ib:

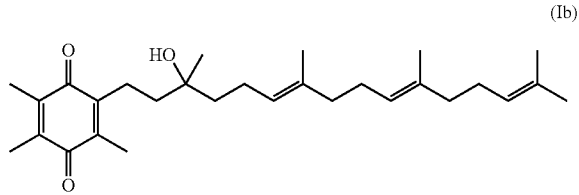 [SMILES: CC(C)=CCC/C(C)=C/CC/C(C)=C/CCC(C)(O)CCC1=C(C)C(=O)C(C)=C(C)C1=O]

(Ib)

which is named 2-(3-hydroxy-3,7,11,15-tetramethylhexadeca-6,10,14-trienyl)-3,5,6-trimethylcyclohexa-2,5-diene-14-dione;
and all salts, stereoisomers, mixtures of stereoisomers, prodrugs, metabolites, solvates and hydrates thereof. In particular, the stereoisomers 2-(3R,6E,10E)-3-hydroxy-3,7,11,15-tetramethylhexadeca-6,10-dienyl)-3,5,6-trimethylcyclohexa-2,5-diene-1,4-dione and 2-((3S,6E,10E)-3-hydroxy-3,7,11,15-tetramethylhexadeca-6,10-dienyl)-3,5,6-trimethylcyclohexa-2,5-diene-1,4-dione (abbreviated as Ib-R and Ib-S, respectively) are included in this embodiment.

In another embodiment, the invention embraces a method of reducing the symptoms associated with, or of treating or suppressing autistic spectrum disorder (ASD) in a patient in need of such treatment by administering a therapeutically or physiologically effective amount of a compound of Formula Ib:

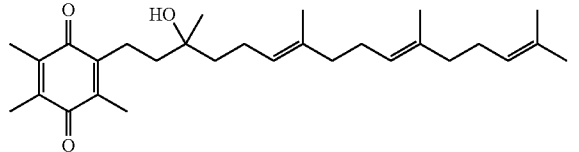

(Ib)

and all salts, stereoisomers, mixtures of stereoisomers, prodrugs, metabolites, solvates and hydrates thereof, such as Ib-R and Ib-S.

In another embodiment, the invention embraces a method of reducing the symptoms associated with, or of treating or suppressing autism in a patient in need of such treatment by administering a therapeutically or physiologically effective amount of a compound of Formula Ib:

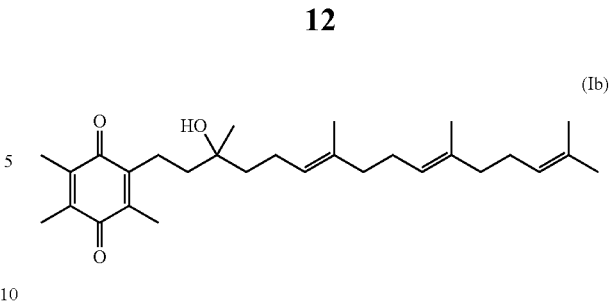

(Ib)

and all salts, stereoisomers, mixtures of stereoisomers, prodrugs, metabolites, solvates and hydrates thereof, such as Ib-R and Ib-S.

In another embodiment, the invention embraces a method of reducing the symptoms associated with, or of treating or suppressing attention deficit/hyperactivity disorder (ADHD) in a patient in need of such treatment by administering a therapeutically or physiologically effective amount of a compound of Formula Ib:

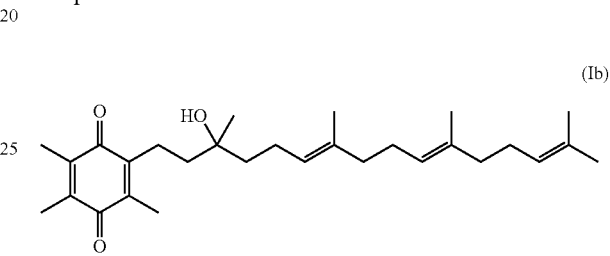

(Ib)

and all salts, stereoisomers, mixtures of stereoisomers, prodrugs, metabolites, solvates and hydrates thereof, such as Ib-R and Ib-S.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of a compound of Formula Ic:

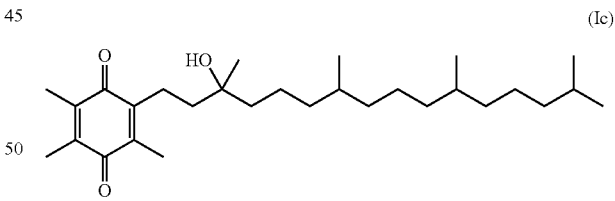

(Ic)

which is named 2-(3-hydroxy-3,7,11,15-tetramethylhexadecyl)-3,5,6-trimethylcyclohexa-2,5-diene-1,4-dione; and all salts, stereoisomers, mixtures of stereoisomers, prodrugs, metabolites, solvates and hydrates thereof. In particular, the stereoisomers 2-((3R,7R,11R)-3-hydroxy-3,7,11,15-tetramethylhexadecyl)-3,5,6-trimethylcyclohexa-2,5-diene-1,4-dione; 2-((3S,7R,11R)-3-hydroxy-3,7,11,15-tetramethylhexadecyl)-3,5,6-trimethylcyclohexa-2,5-diene-1,4-dione; 2-((3R,7S,11R)-3-hydroxy-3,7,11,15-tetramethylhexadecyl)-3,5,6-trimethylcyclohexa-2,5-diene-1,4-dione; 2-(3R,7R,11S)-3-hydroxy-3,7,11,15-tetramethylhexadecyl)-3,5,6-trimethylcyclohexa-2,5-diene-1,4-dione; 2-((3S,7S,11R)-3-hydroxy-3,7,11,15-tetramethylhexadecyl)-3,5,6-trimethylcyclohexa-2,5-diene-1,4-dione; 2-((3S,7R,11S)-3- hydroxy-3,7,11,15-tetramethylhexadecyl)-3,5,6-trimethylcyclohexa-2,5-diene-1,4-dione; 2-((3R,7S,11S)-3-hydroxy-3,7,11,15-tetramethylhexadecyl)-3,5,6-trimethylcyclohexa-2,5-diene-1,4-dione; and 2-((3S,7S,11S)-3-hydroxy-3,7,11,15-tetramethylhexadecyl)-3,5,6-trimethylcyclohexa-2,5-diene-1,4-dione; (referred to as Ic-RRR, Ic-SRR, Ic-RSR, Ic-SSR, Ic-RSS, and Ic-SSS, respectively) are included in this embodiment.

In another embodiment, the invention embraces a method of reducing the symptoms associated with, or of treating or suppressing an autistic spectrum disorder (ASD) in a patient in need of such treatment by administering a therapeutically or physiologically effective amount of a compound of Formula Ic:

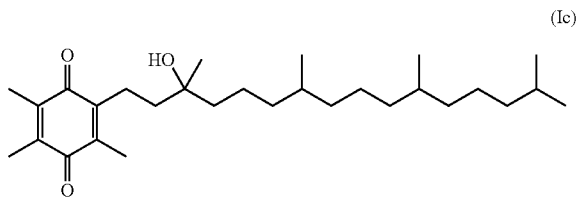 [SMILES: CC1=C(C)C(=O)C(CCC(C)(O)CCCC(C)CCCC(C)CCCC(C)C)=C(C)C1=O]

(Ic)

and all salts, stereoisomers, mixtures of stereoisomers, prodrugs, metabolites, solvates and hydrates thereof, such as Ic-RRR, Ic-SRR, Ic-RSR, Ic-RSS, Ic-SSR, Ic-SRS, Ic-RSS, and Ic-SSS.

In another embodiment, the invention embraces a method of reducing the symptoms associated with, or of treating or suppressing autism in a patient in need of such treatment by administering a therapeutically or physiologically effective amount of a compound of Formula Ic:

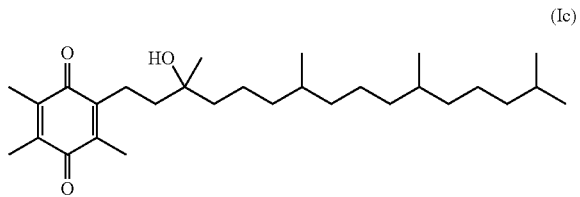 [SMILES: CC1=C(C)C(=O)C(CCC(C)(O)CCCC(C)CCCC(C)CCCC(C)C)=C(C)C1=O]

(Ic)

and all salts, stereoisomers, mixtures of stereoisomers, prodrugs, metabolites, solvates and hydrates thereof, such as Ic-RRR, Ic-SRR, Ic-RSR, Ic-RRS, Ic-SSR, Ic-SRS, Ic-RSS, and Ic-SSS.

In another embodiment, the invention embraces a method of reducing the symptoms associated with, or of treating or suppressing attention deficit/hyperactivity disorder (ADHD) in a patient in need of such treatment by administering a therapeutically or physiologically effective amount of a compound of Formula Ic:

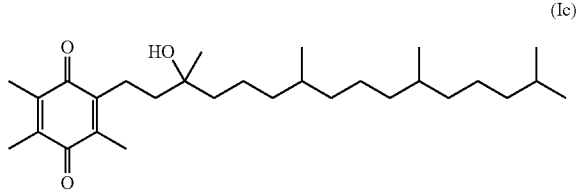 [SMILES: CC1=C(C)C(=O)C(CCC(C)(O)CCCC(C)CCCC(C)CCCC(C)C)=C(C)C1=O]

(Ic)

and all salts, stereoisomers, mixtures of stereoisomers, prodrugs, metabolites, solvates and hydrates thereof, such as Ic-RRR, Ic-SRR, Ic-RSR, Ic-RRS, Ic-SSR, Ic-SRS, Ic-RSS, and Ic-SSS.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of one or more compounds of Formula IIId, Formula IVd or mixtures thereof,

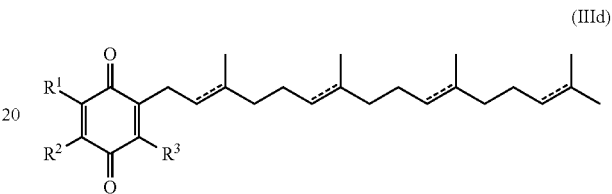

(IIId)

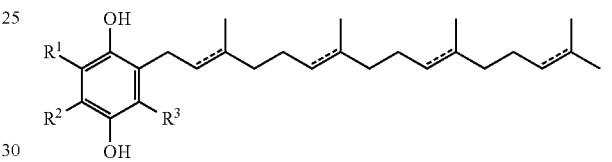

(IVd)

wherein,
the bonds indicated with a dashed line can independently be single or double, $R^1$, $R^2$, and $R^3$ are independently selected from H, $(C_1-C_6)$alkyl, and $(C_1-C_6)$alkoxy; and all salts, stereoisomers, mixtures of stereoisomers, prodrugs, metabolites, solvates and hydrates thereof. In another embodiment, the bonds indicated with a dashed line are all single bonds. In another embodiment, the bonds indicated with a dashed line are all double bonds.

In one embodiment, $R^1$, $R^2$, and $R^3$ are independently selected from $(C_1-C_4)$alkyl, and in a particular example $R^1$, $R^2$, and $R^3$ are methyl. In another embodiment, at least one of $R^1$, $R^2$, and $R^3$ is not methyl. In another embodiment, $R^1$ and $R^2$ are independently selected from $(C_1-C_4)$alkoxy, and $R^3$ is $(C_1-C_4)$alkyl. In another embodiment, $R^1$ and $R^2$ are methoxy, and $R^3$ is methyl.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of a compound of Formula IIIb:

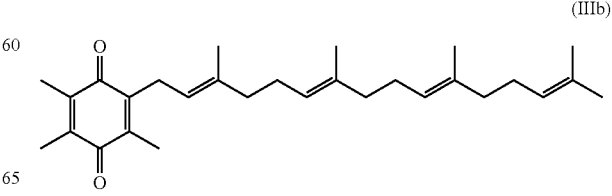

(IIIb)

which is named 2,3,5-trimethyl-6-(3,7,11,15-tetramethylhexadeca-2,6,10,14-tetraenyl)cyclohexa-2,5-diene-1,4-dione; and all salts, stereoisomers, mixtures of stereoisomers, prodrugs, metabolites, solvates and hydrates thereof.

In another embodiment, the invention embraces a method of reducing the symptoms associated with, or of treating or suppressing an autistic spectrum disorder (ASD) in a patient in need of such treatment by administering a therapeutically or physiologically effective amount of a compound of Formula IIIb:

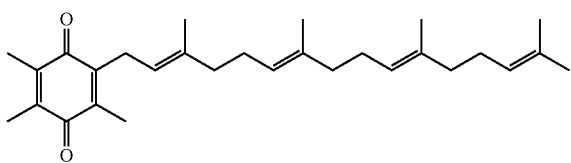

(IIIb)

and all salts, stereoisomers, mixtures of stereoisomers, prodrugs, metabolites, solvates and hydrates thereof.

In another embodiment, the invention embraces a method of reducing the symptoms associated with, or of treating or suppressing autism in a patient in need of such treatment by administering a therapeutically or physiologically effective amount of a compound of Formula IIIb:

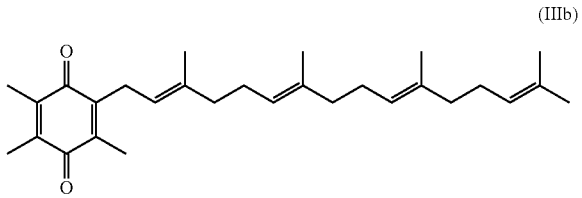 [SMILES: CC(C)=CCC/C(C)=C/CC/C(C)=C/CC/C(C)=C/CC1=C(C)C(=O)C(C)=C(C)C1=O]

(IIIb)

and all salts, stereoisomers, mixtures of stereoisomers, prodrugs, metabolites, solvates and hydrates thereof.

In another embodiment, the invention embraces a method of reducing the symptoms associated with, or of treating or suppressing attention deficit/hyperactivity disorder (ADHD) in a patient in need of such treatment by administering a therapeutically or physiologically effective amount of a compound of Formula IIIb:

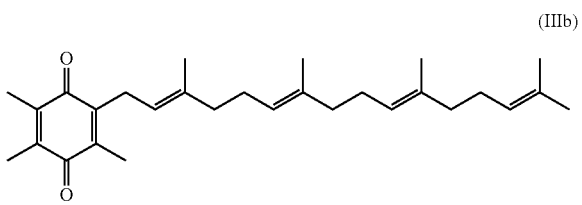 [SMILES: CC(C)=CCC/C(C)=C/CC/C(C)=C/CC/C(C)=C/CC1=C(C)C(=O)C(C)=C(C)C1=O]

(IIIb)

and all salts, stereoisomers, mixtures of stereoisomers, prodrugs, metabolites, solvates and hydrates thereof.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of a compound of Formula IIIc:

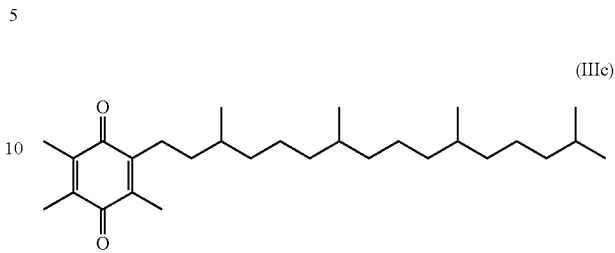

(IIIc)

which is named 2,3,5-trimethyl-6-(3,7,11,15-tetramethylhexadecyl)cyclohexa-2,5-diene-1,4-dione; and all salts, stereoisomers, mixtures of stereoisomers, prodrugs, metabolites, solvates and hydrates thereof. In particular, the stereoisomers 2,3,5-trimethyl-6-((3R,7R,11R)-3,7,11,15-tetramethylhexadecyl)cyclohexa-2,5-diene-1,4-dione; 2,3,5-trimethyl-6-((3S,7R,11R)-3,7,11,15-tetramethylhexadecyl)cyclohexa-2,5-diene-1,4-dione; 2,3,5-trimethyl-6-((3R,7S,11R)-3,7,11,15-tetramethylhexadecyl)cyclohexa-2,5-diene-1,4-dione; 2,3,5-trimethyl-6-((3R,7R,11S)-3,7,11,15-tetramethylhexadecyl)cyclohexa-2,5-diene-1,4-dione; 2,3,5-trimethyl-6-((3S,7S,11R)-3,7,11,15-tetramethylhexadecyl)cyclohexa-2,5-diene-1,4-dione; 2,3,5-trimethyl-6-((3S,7R,11S)-3,7,11,15-tetramethylhexadecyl)cyclohexa-2,5-diene-1,4-dione; 2,3,5-trimethyl-6-((3R,7S,11S)-3,7,11,15-tetramethylhexadecyl)cyclohexa-2,5-diene-1,4-dione; and 2,3,5-trimethyl-6-((3S,7S,11S)-3,7,11,15-tetramethylhexadecyl)cyclohexa-2,5-diene-1,4-dione (abbreviated as IIIc-RRR, IIIc-SRR, IIIc-RSR, IIIc-RRS, IIIc-SSR, IIIc-SRS, IIIc-RSS, and IIIc-SSS, respectively) are included in this embodiment.

In another embodiment, the invention embraces a method of reducing the symptoms associated with, or of treating or suppressing an autistic spectrum disorder (ASD) in a patient in need of such treatment by administering a therapeutically or physiologically effective amount of a compound of Formula IIIc:

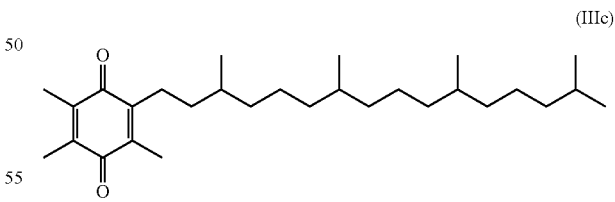

(IIIc)

and all salts, stereoisomers, mixtures of stereoisomers, prodrugs, metabolites, solvates and hydrates thereof, such IIIc-RRR, IIIc-SRR, IIIc-RSR, IIIc-RRS, IIIc-SSR, IIIc-SRS, and IIIc-SSS.

In another embodiment, the invention embraces a method of reducing the symptoms associated with, or of treating or suppressing autism in a patient in need of such treatment by administering a therapeutically or physiologically effective amount of a compound of Formula IIIc:

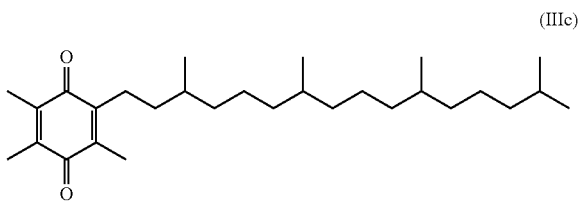 [SMILES: CC1=C(C)C(=O)C(CCC(C)CCCC(C)CCCC(C)CCCC(C)C)=C(C)C1=O]

(IIIc)

and all salts, stereoisomers, mixtures of stereoisomers, prodrugs, metabolites, solvates and hydrates thereof, such as IIIc-RRR, IIIc-SRR, IIIc-RSR, IIIc-RRS, IIIc-SSR, IIIc-SRS, IIIc-RSS, and IIIc-SSS.

In another embodiment, the invention embraces a method of reducing the symptoms associated with, or of treating or suppressing attention deficit/hyperactivity disorder (ADHD) in a patient in need of such treatment by administering a therapeutically or physiologically effective amount of a compound of Formula IIIc:

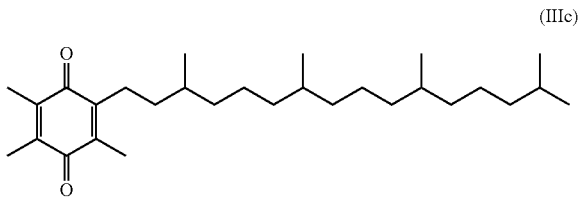 [SMILES: CC1=C(C)C(=O)C(CCC(C)CCCC(C)CCCC(C)CCCC(C)C)=C(C)C1=O]

(IIIc)

and all salts, stereoisomers, mixtures of stereoisomers, prodrugs, metabolites, solvates and hydrates thereof, such as IIIc-RRR, IIIc-SRR, IIIc-RSR, IIIc-RRS, IIIc-SSR, IIIc-SRS, IIIc-RSS, and IIIc-SSS.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of a compound of Formula Va or Formula VIa or mixtures thereof:

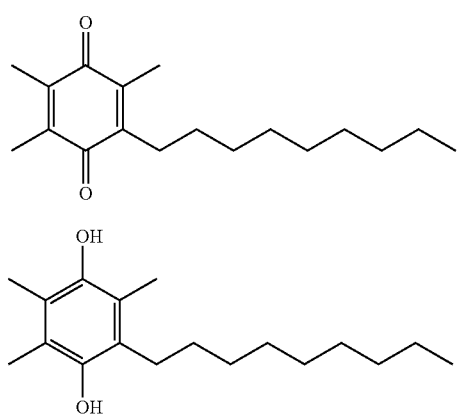

(Va)

(VIa)

and all salts, stereoisomers, mixtures of stereoisomers, prodrugs, metabolites, solvates and hydrates thereof.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD) in a patient in need of such treatment by administering a therapeutically or physiologically effective amount of a compound of Formula Va:

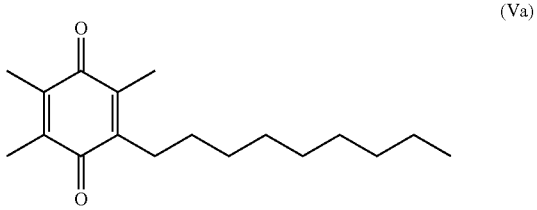 [SMILES: CCCCCCCCCC1=C(C)C(=O)C(C)=C(C)C1=O]

(Va)

which is named 2,3,5-trimethyl-6-nonylcyclohexa-2,5-diene-1,4-diene; and all salts, stereoisomers, mixtures of stereoisomers, prodrugs, metabolites, solvates and hydrates thereof.

In another aspect, the invention embraces a method of reducing the symptoms associated with, or of treating or suppressing an autistic spectrum disorder (ASD) in a patient in need of such treatment by administering a therapeutically or physiologically effective amount of a compound of Formula Va:

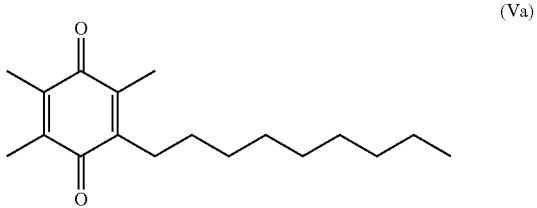 [SMILES: CCCCCCCCCC1=C(C)C(=O)C(C)=C(C)C1=O]

(Va)

and all salts, stereoisomers, mixtures of stereoisomers, prodrugs, metabolites, solvates and hydrates thereof.

In another aspect, the invention embraces a method of reducing the symptoms associated with, or of treating or suppressing autism in a patient in need of such treatment by administering a therapeutically or physiologically effective amount of a compound of Formula Va:

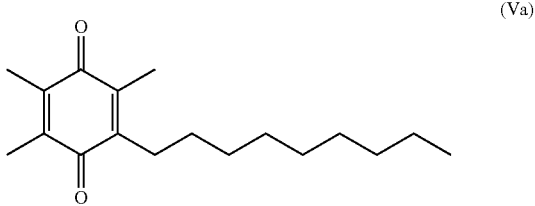 [SMILES: CCCCCCCCCC1=C(C)C(=O)C(C)=C(C)C1=O]

(Va)

and all salts, stereoisomers, mixtures of stereoisomers, prodrugs, metabolites, solvates and hydrates thereof.

In another aspect, the invention embraces a method of reducing the symptoms associated with, or of treating or suppressing attention deficit/hyperactivity disorder (ADHD) in a patient in need of such treatment by administering a therapeutically or physiologically effective amount of a compound of Formula Va:

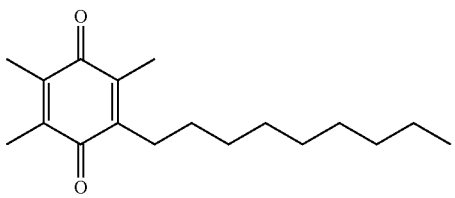

(Va)

and all salts, stereoisomers, mixtures of stereoisomers, prodrugs, metabolites, solvates and hydrates thereof.

In another embodiment the invention embraces a composition wherein the compound is selected from 2-(3-hydroxy-3,7,11,15-tetramethylhexadeca-6,10,14-trienyl)-3,5,6-trimethylcyclohexa-2,5-diene-1,4-dione (Ib); Ib-R; Ib-S; 2-(3-hydroxy-3,7,11,15-tetramethylhexadecyl)-3,5,6-trimethylcyclohexa-2,5-diene-1,4-dione (Ic); Ic-RRR; Ic-SRR; Ic-RSR; Ic-RRS; Ic-SSR; Ic-SRS; Ic-RSS; Ic-SSS; 2,3,5-trimethyl-6-(3,7,11,15-tetramethylhexadeca-2,6,10,14-tetraenyl)cyclohexa-2,5-diene-1,4-dione 2,3,5-trimethyl-6-(3,7,11,15-tetramethylhexadecyl)cyclohexa-2,5-diene-1,4-dione (IIIc); IIIc-RRR; IIIc-SRR; IIIc-RSR; IIIc-RRS; IIIc-SSR; IIIc-SRS; IIIc-RSS; IIIc-SSS; and 2,3,5-trimethyl-6-nonylcyclohexa-2,5-diene-1,4-dione.

In another embodiment, the invention embraces a method of reducing the symptoms associated with, or of treating or suppressing pervasive developmental disorder (PDD), including autistic disorder, Asperger's syndrome, childhood disintegrative disorder (CDD), Rett's disorder, and PDD-not otherwise specified (PDD-NOS) or attention deficit/hyperactivity disorder (ADHD), in a patient in need of such treatment by administering a therapeutically or physiologically effective amount of one or more compounds selected from 2-(3-hydroxy-3,7,11,15-tetramethylhexadeca-6,10,14-trienyl)-3,5,6-trimethylcyclohexa-2,5-diene-1,4-dione (Ib); Ib-R; Ib-S; 2-(3-hydroxy-3,7,11,15-tetramethylhexadecyl)-3,5,6-trimethylcyclohexa-2,5-diene-1,4-dione (Ic); Ic-RRR; Ic-SRR; Ic-RSR; Ic-RRS; Ic-SSR; Ic-SRS; Ic-RSS; Ic-SSS; 2,3,5-trimethyl-6-(3,7,11,15-tetramethylhexadeca-2,6,10,14-tetraenyl)cyclohexa-2,5-diene-1,4-dione (III-b); 2,3,5-trimethyl-6-(3,7,11,15-tetramethylhexadecyl)cyclohexa-2,5-diene-1,4-dione (IIIc); IIIc-RRR; IIIc-SRR; IIIc-RSR; IIIc-RRS; IIIc-SSR; IIIc-SRS; IIIc-RSS; IIIc-SSS; and 2,3,5-trimethyl-6-nonylcyclohexa-2,5-diene-1,4-dione.

In another embodiment, the invention embraces a method of reducing the symptoms associated with, or of treating or suppressing an autistic spectrum disorder (ASD) in a patient in need of such treatment by administering a therapeutically or physiologically effective amount of one or more compounds selected from 2-(3-hydroxy-3,7,11,15-tetramethylhexadeca-6,10,14-trienyl)-3,5,6-trimethylcyclohexa-2,5-diene-1,4-dione (Ib); Ib-R; Ib-S; 2-(3-hydroxy-3,7,11,15-tetramethylhexadecyl)-3,5,6-trimethylcyclohexa-2,5-diene-1,4-dione (Ic); Ic-RRR; Ic-SRR; Ic-RSR; Ic-RRS; Ic-SSR; Ic-SRS; Ic-RSS; Ic-SSS; 2,3,5-trimethyl-6-(3,7,11,15-tetramethylhexadeca-2,6,10,14-tetraenyl)cyclohexa-2,5-diene-1,4-dione (III-b); 2,3,5-trimethyl-6-(3,7,11,15-tetramethylhexadecyl)cyclohexa-2,5-diene-1,4-dione (IIIc); IIIc-RRR; IIIc-SRR; IIIc-RSR; IIIc-RRS; IIIc-SSR; IIIc-SRS; IIIc-RSS; IIIc-SSS; and 2,3,5-trimethyl-6-nonylcyclohexa-2,5-diene-1,4-dione.

In another embodiment, the invention embraces a method of reducing the symptoms associated with, or of treating or suppressing autism in a patient in need of such treatment by administering a therapeutically or physiologically effective amount of one or more compounds selected from 2-(3-hydroxy-3,7,11,15-tetramethylhexadeca-6,10,14-trienyl)-3,5,6-trimethylcyclohexa-2,5-diene-1,4-dione (Ib); Ib-R; Ib-S; 2-(3-hydroxy-3,7,11,15-tetramethylhexadecyl)-3,5,6-trimethylcyclohexa-2,5-diene-1,4-dione (Ic); Ic-RRR; Ic-SRR; Ic-RSR; Ic-RRS; Ic-SSR; Ic-SRS; Ic-RSS; Ic-SSS; 2,3,5-trimethyl-6-(3,7,11,15-tetramethylhexadeca-2,6,10,14-tetraenyl)cyclohexa-2,5-diene-1,4-dione (III-b); 2,3,5-trimethyl-6-(3,7,11,15-tetramethylhexadecyl)cyclohexa-2,5-diene-1,4-dione (IIIc); IIIc-RRR; IIIc-SRR; IIIc-RSR; IIIc-RRS; IIIc-SSR; IIIc-SRS; IIIc-RSS; IIIc-SSS; and 2,3,5-trimethyl-6-nonylcyclohexa-2,5-diene-1,4-dione.

In another embodiment, the invention embraces a method of reducing the symptoms associated with, or of treating or suppressing attention deficit/hyperactivity disorder (ADHD) in a patient in need of such treatment by administering a therapeutically or physiologically effective amount of one or more compounds selected from 2-(3-hydroxy-3,7,11,15-tetramethylhexadeca-6,10,14-trienyl)-3,5,6-trimethylcyclohexa-2,5-diene-1,4-dione (Ib); Ib-R; Ib-S; 2-(3-hydroxy-3,7,11,15-tetramethylhexadecyl)-3,5,6-trimethylcyclohexa-2,5-diene-1,4-dione (Ic); Ic-RRR; Ic-SRR; Ic-RSR; Ic-RRS; Ic-SSR; Ic-SRS; Ic-RSS; Ic-SSS; 2,3,5-trimethyl-6-(3,7,11,15-tetramethylhexadeca-2,6,10,14-tetraenyl)cyclohexa-2,5-diene-1,4-dione (III-b); 2,3,5-trimethyl-6-(3,7,11,15-tetramethylhexadecyl)cyclohexa-2,5-diene-1,4-dione (IIIc); IIIc-RRR; IIIc-SRR; IIIc-RSR; IIIc-RRS; IIIc-SSR; IIIc-SRS; IIIc-RSS; IIIc-SSS; and 2,3,5-trimethyl-6-nonylcyclohexa-2,5-diene-1,4-dione.

In another embodiment, the invention embraces the use of one or more compounds of Formula I, Formula II, Formula III, Formula IV, Formula V, Formula VI, or mixtures thereof,

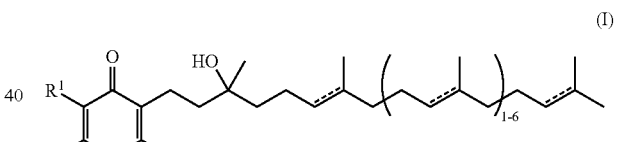

(I)

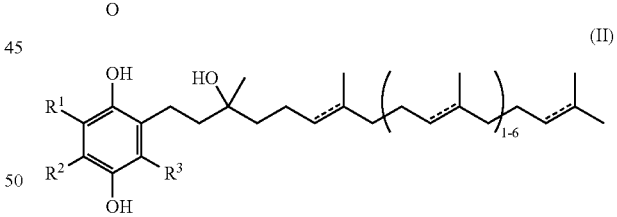

(II)

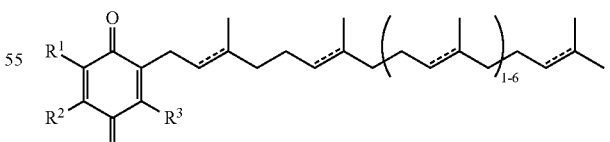

(III)

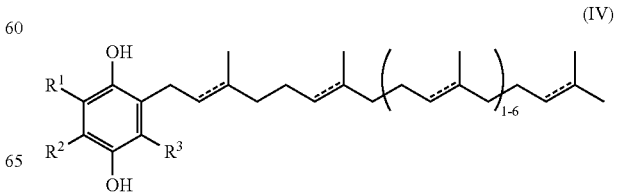

(IV)

-continued (V)

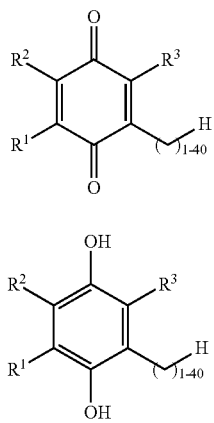

(VI)

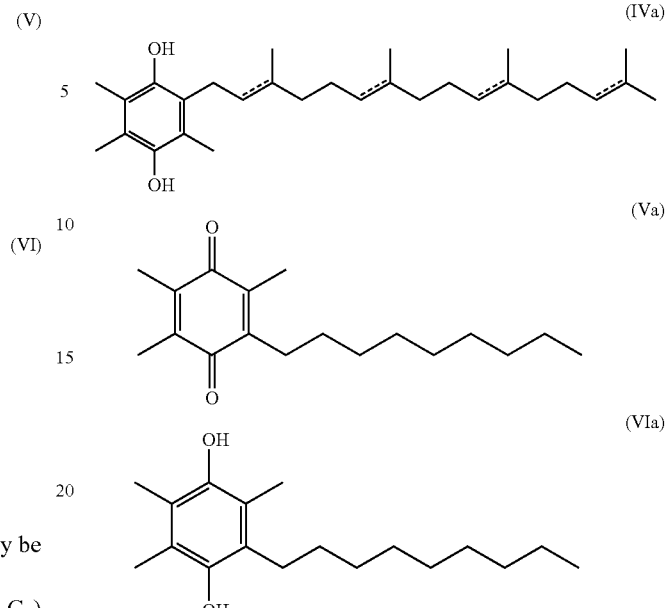

wherein,
the bonds indicated with a dashed line can independently be single or double;
$R^1$, $R^2$, and $R^3$ are independently selected from H, $(C_1-C_6)$ alkyl, $(C_1-C_6)$haloalky $(C_1-C_6)$alkoxy, halogen and CN;
and all salts, stereoisomers, mixtures of stereoisomers, prodrugs, metabolites, solvates and hydrates thereof; for reducing the symptoms associated with, or for treating or suppressing pervasive developmental disorders (PDDs) in a patient in need of such treatment. In another embodiment, the bonds indicated with a dashed line are all single bonds. In another embodiment, the bonds indicated with a dashed line are all double bonds.

In another embodiment, the invention embraces the use of one or more compounds of Formula Ia, Formula IIa, Formula IIIa, Formula IVa, Formula Va, Formula VIa, or mixtures thereof, (Ia)

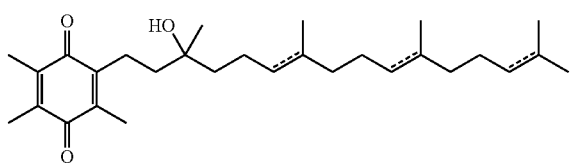

(IIa)

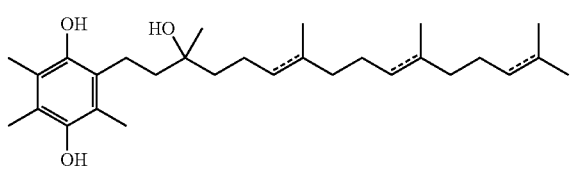

(IIIa)

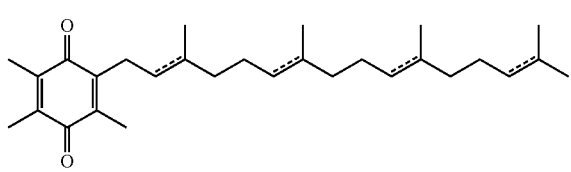

and all salts, stereoisomers, mixtures of stereoisomers, prodrugs, metabolites, solvates and hydrates thereof; for reducing the symptoms associated with, or for treating or suppressing pervasive developmental disorders (PDDs) in a patient in need of such treatment. In another embodiment, the bonds indicated with a dashed line are all single bonds. In another embodiment, the bonds indicated with a dashed line are all double bonds.

In another embodiment, the invention embraces the use of one or more compounds selected from 2-(3-hydroxy-3,7,11,15-tetramethylhexadeca-6,10,14-trienyl)-3,5,6-trimethylcyclohexa-2,5-diene-1,4-dione (Ib); Ib-R; Ib-S; 2-(3-hydroxy-3,7,11,15-tetramethylhexadecyl)-3,5,6-trimethylcyclohexa-2,5-diene-1,4-dione (Ic); Ic-RRR; Ic-SRR; Ic-RSR; Ic-RRS; Ic-SSR; Ic-SRS; Ic-RSS; Ic-SSS; 2,3,5-trimethyl-6-(3,7,11,15-tetramethylhexadeca-2,6,10,14-tetraenyl)cyclohexa-2,5-diene-1,4-dione (III-b); 2,3,5-trimethyl-6-(3,7,11,15-tetramethylhexadecyl)cyclohexa-2,5-diene-1,4-dione (IIIc); IIIc-RRR; IIIc-SRR; IIIc-RSR; IIIc-RRS; IIIc-SSR; IIIc-SRS; IIIc-RSS; IIIc-SSS; and 2,3,5-trimethyl-6-nonylcyclohexa-2,5-diene-1,4-dione for reducing the symptoms associated with, or for treating or suppressing pervasive developmental disorders (PDDs) in a patient in need of such treatment.

In any of the foregoing embodiments, the pervasive developmental disorder (PDD) can be selected from autistic spectrum disorder (ASD).

In any of the foregoing embodiments, the disorder can be attention deficit/hyperactivity disorder (ADHD)

In any of the foregoing embodiments, the symptoms treated by the compounds of the present invention are selected from the group of symptoms consisting of eye contact avoidance, failure to socialize, attention deficit, poor mood, hyperactivity, anxiety, stimming, poor comprehension, inappropriate speech, abnormal sound sensitivity, poor digestion, disrupted sleep, and perseveration, and where the decreased incidence is measured relative to the incidence in the untreated individual.

In one embodiment, the present invention provides pharmaceutical compositions able to reduce the symptoms of autism in a patient, comprising a physiologically effective amount of one or more compounds of Formula I, Formula II, Formula III, Formula IV, Formula V, Formula VI, Formula Ia, Formula IIa, Formula IIIa, Formula IVa, Formula Va, Formula VIa, Formula Ib, Formula Ib-R, Formula Ib-S, Formula Ic, Formula Ic-RRR, Formula Ic-SRR, Formula Ic-RSR, Formula Ic-RRS, Formula Ic-SSR, Formula Ic-SRS, Formula Ic-RSS, Formula Ic-SSS, Formula IIIb, Formula IIIc, Formula IIIc-RRR, Formula IIIc-SRR, Formula IIIc-RSR, Formula IIIc-RRS, Formula IIIc-SSR, Formula IIIc-SRS, Formula IIIc-RSS, Formula IIIc-SSS, Formula Formula IId, Formula IIId, or Formula IVd, and at least one of the group consisting of a physiologically acceptable carrier, adjuvant, excipient, buffer and diluent.

In still a further aspect, the present invention provides foods, medical foods, functional foods, food supplements, or dietary supplements comprising compositions of one or more compounds of Formula I, Formula II, Formula III, Formula IV, Formula V, Formula VI, Formula Ia, Formula IIa, Formula IIIa, Formula IVa, Formula Va, Formula VIa, Formula Ib, Formula Ib-R, Formula Ib-S, Formula Ic, Formula Ic-RRR, Formula Ic-SRR, Formula Ic-RSR, Formula Ic-RRS, Formula Ic-SSR, Formula Ic-SRS, Formula Ic-RSS, Formula Ic-SSS, Formula IIIb, Formula IIIc, Formula IIIc-RRR, Formula IIIc-SRR, Formula IIIc-RSR, Formula IIIc-RRS, Formula IIIc-SSR, Formula IIIc-SRS, Formula IIIc-RSS, Formula IIIc-SSS, Formula Formula IId, Formula IIId, or Formula IVd, and at least one of the group consisting of a physiologically or nutritionally acceptable carrier, adjuvant, excipient, buffer and diluent. In one embodiment, the invention comprises a method of administering a therapeutically effective amount or physiologically effective amount of the foods, medical foods, functional foods, food supplements, or dietary supplements to a patient in need thereof. In another embodiment, the invention comprises a method of reducing the symptoms associated with, or for treating or suppressing pervasive developmental disorder (PDD), including autistic disorder, Asperger's syndrome, childhood disintegrative disorder (CDD), Rett's disorder, and PDD-Not Otherwise Specified (PDD-NOS); or attention deficit/hyperactivity disorder (ADHD), by administering a therapeutically effective amount or physiologically effective amount of the foods, medical foods, functional foods, food supplements, or dietary supplements to a patient in need thereof, especially for reducing the symptoms associated with, or for treating or suppressing, autistic spectrum disorder (ASD); or for reducing the symptoms associated with or for treating or suppressing, attention deficit/hyperactivity disorder (ADHD).

In yet another aspect, the invention also provides articles of manufacture and kits containing materials useful for treating or suppressing autistic spectrum disorder. The invention also provides kits comprising any one or more of the compounds of Formula I, Formula II, Formula III, Formula IV, Formula V, Formula VI, Formula Ia, Formula IIa, Formula IIIa, Formula IVa, Formula Va, Formula VIa, Formula Ib, Formula Ib-R, Formula Ib-S, Formula Ic, Formula Ic-RRR, Formula Ic-SRR, Formula Ic-RSR, Formula Ic-RRS, Formula Ic-SSR, Formula Ic-SRS. Formula Ic-RSS, Formula IIIc-SSS, Formula IIIb, Formula IIIc, Formula IIIc-RRR, Formula IIIc-SRR, Formula IIIc-RSR, Formula IIIc-RRS, Formula IIIc-SSR, Formula IIIc-SRS, Formula IIIc-RSS, Formula IIIc-SSS, Formula Id, Formula IId, Formula IIId, or Formula IVd. In some embodiments, the kit of the invention comprises the container described above.

In other aspects, the kits may be used for any of the methods described herein, including, for example, to treat an individual with ASD disorder, or to suppress an ASD disorder in an individual.

In one embodiment, the invention also embraces modulating one or more autism biomarkers, normalizing one or more autism biomarkers, or enhancing one or more autism biomarkers, comprising administering to a subject a therapeutically effective amount or physiologically effective amount of one or more compounds or compositions as described herein. The invention also embraces compounds and compositions as described herein, which are useful for modulating one or more autism biomarkers, normalizing one or more autism biomarkers, or enhancing one or more autism biomarkers.

The present invention comprises multiple aspects, features and embodiments; where such multiple aspects, features and embodiments can be combined and permuted in any desired manner.

These and other aspects, features and embodiments of the present invention will become evident upon reference to the remainder of this application, including the following detailed description. In addition, various references are set forth herein that describe in more detail certain compositions, and/or methods; all such references are incorporated herein by reference in their entirety.

DETAILED DESCRIPTION OF THE INVENTION

The present invention provides methods and compositions able to reduce the symptoms of pervasive developmental disorder including autistic spectrum disorder or attention deficit/hyperactivity disorder (AMID) in a patient, including a human patient. Briefly, the compositions and methods comprise administering a compound of Formula I, Formula II, Formula III, Formula IV, Formula V, Formula VI, Formula Ia, Formula IIa, Formula IIIa, Formula IVa, Formula Va, Formula VIa, Formula Ib, Formula Ib-R, Formula Ib-S, Formula Ic, Formula Ic-RRR, Formula Ic-SRR, Formula Ic-RSR, Formula Ic-RRS, Formula Ic-SSR, Formula Ic-SRS, Formula Ic-RSS, Formula Ic-SSS, Formula IIIb, Formula III, Formula IIIc-RRR, Formula IIIc-SRR, Formula IIIc-RSR, Formula IIIc-RRS, Formula IIIc-SSR, Formula IIIc-SRS, Formula IIIc-RSS, Formula IIIc-SSS, Formula Id, Formula IId, Formula IIId, or Formula IVd to a human patient in sufficient quantities to reduce the effects of the autistic disease or of the attention deficit disorder. An initial trial wherein compounds of Formula I, Formula II, Formula III, Formula IV, Formula V, Formula VI, Formula Ia, Formula IIa, Formula IIIa, Formula IVa, Formula Va, Formula VIa, Formula Ib, Formula Ib-R, Formula Ib-S, Formula Ic, Formula Ic-RRR, Formula Ic-SRR, Formula Ic-RSR, Formula Ic-RRS, Formula Ic-SSR, Formula Ic-SRS, Formula Ic-RSS, Formula Ic-SSS, Formula IIIb, Formula IIIc, Formula IIIc-RRR, Formula IIIc-SRR, Formula IIIc-RSR, Formula IIIc-RRS, Formula IIIc-SSR, Formula IIIc-SRS, Formula IIIc-RSS, Formula IIIc-SSS, Formula Id, Formula IId, Formula IIId, or Formula IVd are administered to human patients, without restriction on the normal diet of the patients, would provide a significant number of the patients with a significant reduction of one or more symptoms, such as increased eye contact, better enunciation and use of pronouns, less fatigue, singing a song for the first time with the melody and words together and the entire song understandable, playing with age appropriate friends for the first time, fewer tantrums, better sleep patterns, improved politeness and coordination, being more loving, acknowledging another individual's emotion, increased voice and word association.

By "subject," "individual," or "patient" is meant an individual, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because the autism disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms.

"Therapeutic use" of the compounds discussed herein is defined as using one or more of the compounds discussed herein to treat or suppress a disease, as defined above. A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations.

A "physiologically effective amount" of an active substance indicates an adequate amount of the active substances to have a significant, externally observable effect on the patient Thus, such a physiologically effective amount affects one or more of the characteristics in the patient without the need for special equipment to determine the effect. For example, a physiologically effective amount of a compound of the present invention has a significant, externally observable effect on the behavior of the patient by reducing one or more of the symptoms of autism or other pervasive developmental disorder. Accordingly, one can determine whether an adequate amount of the active substance has been administered by watching the patient and observing whether changes have occurred in the patient due to the active substance.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes all stereoisomers of the compounds, including diastereomers and enantiomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, *Design of Prodrugs*, New York: Elsevier, 1985; in R. Silverman, *The Organic Chemistry of Drug Design and Drug Action*, Boston: Elsevier, 2004; in R. L. Juliano (ed.), *Biological Approaches to the Controlled Delivery of Drugs* (Annals of the New York Academy of Sciences, v. 507), New York: New York Academy of Sciences, 1987; and in E. B. Roche (ed.), *Design of Biopharmaceutical Properties Through Prodrugs and Analogs* (Symposium sponsored by Medicinal Chemistry Section. APhA Academy of Pharmaceutical Sciences, November 1976 national meeting, Orlando, Fla.), Washington: The Academy, 1977.

Metabolites of the compounds are also embraced by the invention.

"$C_1$-$C_6$ alkyl" is intended to embrace a saturated linear, branched, cyclic, or a combination thereof, hydrocarbon of 1 to 6 carbon atoms. Examples of "$C_1$-$C_6$ alkyl" are methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl, cyclopentyl, hexyl, and cyclohexyl, where the point of attachment of the alkyl group to the remainder of the molecule can be at any chemically possible location on the alkyl fragment. "$C_1$-$C_4$ alkyl" is intended to embrace a saturated linear, branched, cyclic, or a combination thereof, hydrocarbon of 1 to 4 carbon atoms. Examples of "$C_1$-$C_4$ alkyl" are methyl, ethyl, n-propyl, isopropyl, cyclopropyl, n-butyl, isobutyl, sec-butyl, t-butyl, cyclobutyl.

"Halogen" or "halo" designates fluoro, chloro, bromo, and iodo.

"$C_1$-$C_6$ haloalkyl" is intended to embrace any $C_1$-$C_6$ alkyl substituent having at least one halogen substituent; the halogen can be attached via any valence on the $C_1$-$C_6$ alkyl group. Some examples of $C_1$-$C_6$ haloalkyl are —$CF_3$, —$CCl_3$, —$CHF_2$, —$CHCl_2$, —$CHBr_2$, —$CH_2F$, —$CH_2Cl$.

In a first aspect, the present invention provides redox-active compositions that are able to reduce the symptoms of Pervasive Developmental Disorder (PDD), including of Autistic Disorder, Asperger's syndrome, Childhood Disintegrative Disorder (CDD), Rett's Disorder, and PDD-not otherwise specified (PDD-NOS) or attention deficit/hyperactivity disorder (ADHD) in a human patient. For example, the compositions are able to reduce or improve one or more symptoms, such as increased eye contact, better enunciation and use of pronouns, less fatigue, fewer tantrums, better sleep patterns, improved politeness and coordination, and increased voice and word association. In other words, the compositions are able to produce an adequate reduction of one or more of the observable characteristics of autism by an amount that is observable to a human observer, such as a parent, physician or caretaker, without the use of special devices such as microscopes or chemical analytical devices. The compositions reduce such symptoms by providing a physiologically effective amount of one or more compounds of Formula I, Formula II, Formula III, Formula IV, Formula V, Formula VI, Formula Ia, Formula IIa, Formula IIIa, Formula IVa, Formula Va, Formula VIa, Formula Ib, Formula Ib-R, Formula Ib-S, Formula Ic, Formula Ic-RRR, Formula Ic-SRR, Formula Ic-RSR, Formula Ic-RRS, Formula Ic-SSR, Formula Ic-SRS, Formula Ic-RSS, Formula Ic-SSS, Formula IIIb, Formula IIIc, Formula IIIc-RRR, Formula IIIc-SRR, Formula IIIc-RSR, Formula IIIc-RRS, Formula IIIc-SSR, Formula IIIc-SRS, Formula IIIc-RSS, Formula IIIc-SSS, Formula Id, Formula IId, Formula IIId, or Formula IVd, and at least one of the group consisting of a physiologically acceptable carrier, adjuvant, excipient, buffer and diluent, which terms are used in their ordinary sense to indicate substances that assist in the packaging, delivery, absorption, or the physiological effect of the compounds. The physiologically acceptable carriers, adjuvants, excipients, buffers and diluents are preferably nontoxic to recipients at the dosages and concentrations employed. Representative samples include water, isotonic saline solutions that are preferably buffered at physiological pH (such as phosphate-buffered saline or Tris-buffered saline), mannitol, dextrose, glycerol, and ethanol, as well as selected polypeptides or proteins such as human serum albumin, maltodextrin, L-lysine, lactase and other carbohydratases, lipase and non-specific proteases such as papain. The carrier, adjuvant, excipient, buffer, or diluent may be combined with the compositions disclosed herein to provide compositions either as liquid solutions or, preferably, in solid form. For example, when the compositions are to be administered orally, the compositions may be produced in any of powder, tablet or capsule form.

Synthesis of Compounds

The compounds of the present invention can be readily synthesized by a variety of methods known in the art. The synthesis of alpha-tocopherol quinone is detailed in several references, for example in U.S. Pat. No. 3,406,188 and U.S. Pat. No. 4,310,465. The synthesis of benzoquinone type compounds of the present invention is disclosed in co-owned US Patent Application Publication Nos. 2006/0281809, 2007/0072943, and 2007/0225261.

Clinical Assessment of Autism

Carnitine Deficiency:

As documented by Filipek, P A et al, in *J. Autism Dev. Diosrd*. (2004) 34:615-23 serum carnitine levels on 100 children with autism were investigated, concurrently with serum pyruvate, lactate, ammonia, and alanine levels. Values of free and total carnitine (p<0.001), and pyruvate (p=0.006) were significantly reduced while ammonia and alanine levels were considerably elevated (p<0.001) in the autistic subjects. The relative carnitine deficiency in these patients, accompanied by slight elevations in lactate and significant elevations in alanine and ammonia levels, would suggest that assessing pyruvate, lactate, carnitine and ammonia levels may be useful when measured during routine evaluation of ASD children.

Lactic Acid (Lactate) Levels:

Some cases of autism have been associated with abnormal levels of lactic acid, as pyruvate levels increase and pyruvate is converted to lactate to maintain capacity for glycolysis (see Coleman, M. et al. *Journal of Autism and Developmental Disorders* (1985) 15, 1-8.) Lactate levels can be measured by taking samples of appropriate bodily fluids such as whole blood, plasma, or cerebrospinal fluid. Using magnetic resonance, lactate levels can be measured in virtually any volume of the body desired, such as the brain. Whole blood, plasma, and cerebrospinal fluid lactate levels can be measured by commercially available equipment such as the YSI 2300 STAT Plus Glucose & Lactate Analyzer (YSI Life Sciences, Ohio).

Lipid Peroxidation:

Lipid peroxidation has been found to be elevated in autism indicating that oxidative stress is increased in this disease. Lipid peroxidation can be measured by quantifying the levels of malonyldialdehyde (MDA), an end product of fatty acid oxidation. Several assays exist for MDA in plasma, urine, and other specimens. Such assays include specific reagents for UV detection by HPLC (Steghens, J. P., et al., *Free Radic Biol Med* (2001) 31:242 and Pitz, J. *Chromatogr B Biomed Sci appl* (2000) 742:315 and capillary electrophoresis (Korizis, K. N. et al., *Biomed Chromatogr* 15:287 (2001)). A variety of lipid peroxidation products including MDA can be quantified using the thiobarbituric acid reaction (K Fukanaga et al., *Biomed Chromatogr* (1998)12:300).

Lipid peroxidation can also be quantified by measurement of urinary levels of isoprostane F($2\alpha$)-VI, a marker of lipid peroxidation; 2,3-dinor-thromboxane B(2), which reflects platelet activation; and 6-keto-prostaglandin F($1\alpha$), a marker of endothelium activation, by means of gas chromatography-mass spectrometry in subjects with autism and healthy control subjects. Methods of detecting oxidant stress-related products are likewise known in the art. For example, enzyme immunoassay kits are commercially available from Cayman Chemical for determination of isoprostane F($2\alpha$)-VI (Cayman Chemical cat. no. 516301); for 2,3-dinor-thromboxane B(2) (Cayman Chemical cat. no. 519051), and for 6-keto-prostaglandin F($1\alpha$) (Cayman Chemical cat. no. 5152111).

Antioxidant Proteins:

Levels of major antioxidant proteins, namely transferrin (iron binding protein) and ceruloplasmin (copper-binding protein) in the serum, are significantly reduced in autistic children as compared to their developmentally normal non-autistic siblings. A striking correlation was observed between reduced levels of these proteins and loss of previously acquired language skills in children with autism. These results indicate that altered regulation of transferrin and ceruloplasmin in autistic children who lose acquired language skills can be used for diagnosis of disease during evaluation of patients.

In one embodiment, the invention also embraces modulating one or more autism biomarkers, normalizing one or more autism biomarkers, or enhancing one or more autism biomarkers, comprising administering to a subject a therapeutically effective amount or physiologically effective amount of one or more compounds or compositions as described herein. The invention also embraces compounds and compositions as described herein, which are useful for modulating one or more autism biomarkers, normalizing one or more autism biomarkers, or enhancing one or more autism biomarkers.

"Autism biomarkers" include free carnitine levels, total carnitine levels, pyruvate levels, ammonia levels, alanine levels, lactate levels, malonyldialdehyde (MDA) levels, isoprostane $F(2\alpha)$-VI levels, 2,3-dinor-thromboxane $B(2)$ levels. 6-keto-prostaglandin $F(1\alpha)$ levels, transferrin levels and ceruloplasmin levels. These biomarkers can be measured in whole blood, serum, plasma, urine, cerebrospinal fluid, cerebral ventricular fluid, or any other biological samples, bodily fluids, or body compartments.

The compounds and compositions of the invention can be used in subjects or patients to modulate one or more autism biomarkers. Modulation of autism biomarkers can be done to normalize autism biomarkers in a subject, or to enhance autism biomarkers in a subject.

Normalization of one or more autism biomarkers is defined as either restoring the level of one or more such autism biomarkers to normal or near-normal levels in a subject whose levels of one or more autism biomarkers show pathological differences from normal levels (i.e., levels in a healthy subject), or to change the levels of one or more autism biomarkers to alleviate pathological symptoms in a subject. Depending on the nature of the autism biomarker, such levels may show measured values either above or below values in non-autistic subjects. For example, carnitine levels are sometimes reduced in autistic subjects in comparison to non-autistic subjects, and an increase in the carnitine level may be desirable. Ammonia levels are sometimes higher in autistic subjects in comparison to non-autistic subjects, and a decrease in ammonia levels may be desirable. Normalization of autism biomarkers can involve restoring the level of autism biomarkers of an autistic subject to within about at least two standard deviations of the non-autistic value, more preferably to within about at least one standard deviation of the non-autistic value, to within about at least one-half standard deviation of the non-autistic value, or to within about at least one-quarter standard deviation of the non-autistic value.

When an increase in an autism biomarker level is desired to normalize the one or more such autism biomarkers, the level of the autism biomarker in an autistic subject can be increased to within about at least two standard deviations of the value in a non-autistic subject, more preferably increased to within about at least one standard deviation of the non-autistic value, increased to within about at least one-half standard deviation of the non-autistic value, or increased to within about at least one-quarter standard deviation of the non-autistic value, by administration of one or more compounds or compositions according to the invention. Alternatively, the level of one or more of the autism biomarkers can be increased by about at least 10% above the subject's level of the respective one or more autism biomarkers before administration, by about at least 20% above the subject's level of the respective one or more autism biomarkers before administration, by about at least 30% above the subject's level of the respective one or more autism biomarkers before administration, by about at least 40% above the subject's level of the respective one or more autism biomarkers before administration, by about at least 50% above the subject's level of the respective one or more autism biomarkers before administration, by about at least 75% above the subject's level of the respective one or more autism biomarkers before administration, or by about at least 100% above the subject's level of the respective one or more autism biomarkers before administration.

When a decrease in a level of one or more autism biomarkers is desired to normalize the one or more autism biomarkers, the level of the one or more autism biomarkers in an autistic subject can be decreased to a level within about at least two standard deviations of the value in a non-autistic subject, more preferably decreased to within about at least one standard deviation of the value in a non-autistic subject, decreased to within about at least one-half standard deviation of the value in a non-autistic subject, or decreased to within about at least one-quarter standard deviation of the value in a non-autistic subject, by administration of one or more compounds or compositions according to the invention. Alternatively, the level of the one or more autism biomarkers can be decreased by about at least 10% below the subject's level of the respective one or more autism biomarkers before administration, by about at least 20% below the subject's level of the respective one or more autism biomarkers before administration, by about at least 30% below the subject's level of the respective one or more autism biomarkers before administration, by about at least 40% below the subject's level of the respective one or more autism biomarkers before administration, by about at least 50% below the subject's level of the respective one or more autism biomarkers before administration, by about at least 75% below the subject's level of the respective one or more autism biomarkers before administration, or by about at least 90% below the subject's level of the respective one or more autism biomarkers before administration.

Enhancement of the level of one or more autism biomarkers is defined as changing the extant levels of one or more autism biomarkers in an autistic subject to a level which provides beneficial or desired effects for the subject. Additional enhancement, beyond normalization, may be necessary in the event that normalizing the level of one or more autism biomarkers does not suffice to bring about an improvement in symptoms.

Accordingly, when an increase in a level of one or more autism biomarkers is beneficial to an autistic subject, enhancement of the one or more autism biomarkers can involve increasing the level of the respective autism biomarker or autism biomarkers in the autistic subject to about at least one-quarter standard deviation above the value in a non-autistic subject, about at least one-half standard deviation above the value in a non-autistic subject, about at least one standard deviation above the value in a non-autistic subject, or about at least two standard deviations above the value in a non-autistic subject. Alternatively, the level of the one or more autism biomarkers can be increased by about at least 10% above the subject's level of the respective one or more autism biomarkers before enhancement, by about at least 20% above the subject's level of the respective one or more autism biomarkers before enhancement, by about at least 30% above the subject's level of the respective one or more autism biomarkers before enhancement, by about at least 40% above the subject's level of the respective one or more autism biomarkers before enhancement, by about at least 50% above the subject's level of the respective one or more autism biomarkers before enhancement, by about at least 75% above the subject's level of the respective one or more autism biomarkers before enhancement, or by about at least 100% above the subject's level of the respective one or more autism biomarkers before enhancement.

When a decrease in a level of one or more autism biomarkers is desired to enhance one or more autism biomarkers, the level of the one or more autism biomarkers in an autistic subject can be decreased by an amount of about at least one-quarter standard deviation of the value in a non-autistic subject, decreased by about at least one-half standard deviation of the value in a non-autistic subject, decreased by about at least one standard deviation of the value in a non-autistic subject, or decreased by about at least two standard deviations of the value in a non-autistic subject. Alternatively, the level of the one or more autism biomarkers can be decreased by about at least 10% below the subject's level of the respective one or more autism biomarkers before enhancement, by about at least 20% below the subject's level of the respective one or more autism biomarkers before enhancement, by about at least 30% below the subject's level of the respective one or more autism biomarkers before enhancement, by about at least 40% below the subject's level of the respective one or more autism biomarkers before enhancement, by about at least 50% below the subject's level of the respective one or more autism biomarkers before enhancement, by about at least 75% below the subject's level of the respective one or more autism biomarkers before enhancement, or by about at least 90% below the subject's level of the respective one or more autism biomarkers before enhancement.

Pharmaceutical, Nutraceutical and Nutritional Formulations

The compounds described herein can be formulated as pharmaceutical compositions by formulation with additives such as pharmaceutically acceptable excipients, pharmaceutically acceptable carriers, and pharmaceutically acceptable vehicles, or as nutraceutical or nutritional formulations with additives such as nutraceutically or nutritionally acceptable excipients, nutraceutically or nutritionally acceptable carriers, and nutraceutically or nutritionally acceptable vehicles.

Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect. The unit dose may be sufficient as a single dose to have a therapeutic or suppressive effect. Alternatively, the unit dose may be a dose administered periodically in a course of treatment or suppression of a disorder. A unit dose can contain a therapeutically effective amount of a composition disclosed herein. Alternatively, a unit dose can contain a physiologically effective amount of a composition disclosed herein.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compositions, as described above, can be prepared as nutritional formulations such as foods, including medical or functional foods and dietary supplements. A "medical or functional food" is defined as being consumed as part of a usual diet but which has been demonstrated to have physiological benefits and/for to reduce the risk of chronic disease, beyond basic nutritional functions. A "dietary supplement" is defined as a product that is intended to supplement the human diet and is typically provided in the form of a pill, capsule, tablet, or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into food stuffs, such as functional foods designed to promote health or to prevent disease or disorders. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration of the particular formulation can vary based on the individual subject, the stage of disease, and other factors evident to one skilled in the art. During the course of the treatment, the concentration of the subject compositions may be monitored (for example, blood plasma levels may be monitored) to insure that the desired level is maintained.

The term "nutraceutical" has been used to refer to any substance that is a food or a part of a food and provides medical or health benefits, including the prevention and treatment of disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease. Suitable nutraceutically acceptable excipients may include liquid solutions such as a solution comprising a vegetable- and/or animal- and/or fish-derived oil.

Time-release or controlled release delivery systems may be used, such as a diffusion controlled matrix system or an erodible system, as described for example in: Lee. "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, buccally, sublingually, by inhalation (e.g. as mists or sprays), rectally, vaginally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraocular, intraperitoneal, intranasal (e.g. via nasal mucosa), rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cycloclextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

In a preferred embodiment, the compositions are provided to the patient as either a food or a food supplement. For example, when provided as a food the compositions of the present invention are combined with material primarily made up of protein, carbohydrate and/or fat that is used in the body, preferably a human body, to sustain growth, repair, and vital processes, and to furnish energy. When provided as a food supplement, the compositions comprise selected substances such that they can be eaten at or about the same time as a food. The food supplements are generally eaten within about one hour before or after the food is eaten, typically within about one-half hour before or after the food is eaten, preferably within about 15 minutes of when the food is eaten, and further preferably within one to five minutes of the time the food is eaten. The food supplement can also be eaten at the same time as the food, or even with the food.

The invention also provides articles of manufacture and kits containing materials useful for treating or suppressing PDD including Autism or for reducing the symptoms of one or more symptoms of PDD. The invention also provides kits comprising any one or more of the compounds of Formula I, Formula II, Formula III, Formula IV, Formula V, Formula VI, Formula Ia, Formula IIa, Formula IIIa, Formula IVa, Formula Va, Formula VIa, Formula Ib, Formula Ib-R, Formula Ib-S, Formula Ic, Formula Ic-RRR, Formula Ic-SRR, Formula Ic-RSR, Formula RRS, Formula Ic-SSR, Formula Ic-SRS, Formula Ic-RSS, Formula Ic-SSS, Formula IIIb, Formula Inc, Formula IIIc-RRR, Formula IIIc-SRR, Formula IIIc-RSR, Formula IIIc-RRS, Formula IIIc-SSR, Formula IIIc-SRS, Formula IIIc-RSS, Formula IIIc-SSS, Formula Id, Formula IId, Formula IIId, or Formula IVd, or mixtures thereof. In some embodiments, the kit of the invention comprises the container described above.

In other aspects, the kits may be used for any of the methods described herein, including, for example, to treat an individual with a pervasive developmental disorder, including an autistic spectrum disorder, or to suppress a pervasive developmental disorder, such as an autistic spectrum disorder in an individual.

In other aspects, the kits may be used for any of the methods described herein, including, for example, to treat an individual with an attention deficit disorder, including attention deficit/hyperactivity disorder (ADHD), or to suppress an attention deficit disorder, such as attention deficit/hyperactivity disorder (ADHD) in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or physiologically effective amount for a given situation can be readily determined by routine experimentation and is within the skill and judgment of the ordinary clinician.

Examples of dosages which can be used are an effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided, dosage of two, three or four times daily.

While the compounds of the invention can be administered as the sole active pharmaceutical agent, they can also be used in combination with one or more other agents used in the treatment or suppression of disorders. If compounds are administered together, they need not be administered by the same route, or in the same formulation. However, they can be combined into one formulation as desired.

Representative agents useful in combination with the compounds of the invention for the treatment or suppression of PDD, ASD, or ADHD symptoms include, but are not limited to, Coenzyme Q10 and antioxidant compounds and/or drugs, such as but not limited to carnitine, quercetine, mangosteen, acai, uridine, N-acetyl cysteine (NAC), vitamin A, vitamin C, lutein, beta-carotene, lycopene, and glutathione. Other agents useful in combination with the compounds of the invention are compounds and/or drugs that have an effect on the neurotransmitters, particularly serotonin and dopamine, that include antidepressants, anti-anxiety drugs, antispasmodics, neuroleptics and atypical neuroleptics, and stimulants. Antidepressants include but are not limited to Selective Serotonin Reuptake inhibitors (SSRIs) (fluoxetine (Prozac); fluvoxamine (Luvox); paroxetine (Paxil); sertraline (Zoloft); citalopram (Celexa)); Tricyclic antidepressants (amitriptyline (Elavil); amitriptyline/chlordiazepoxide (Limbitrol); amoxapine (Asendin); clomipramine (Anafranil); desipramine (Norpramin); doxepin (Sinequan); imipramine (Tofranil); nortriptyline (Avenytl, Pamelor); protriptyline (Vivactil); trimipramine (Surmontil)); MAO Inhibitors (moclobemide (Aurorex); phenelzine (Nardil); tranylcypromine sulfate (Parnate)); Buproprion; Lithium; Mirtazapine; Nefazodone (Serzone); Reboxetine (Edronax); Venlafaxine (Effexor, Effexor XR); and "natural" anti-depressants such as St. John's Wart. Anti-anxiety drugs include but are not limited to alprazolam (Xanax); chlordiazepoxide (Librium); clonazepam (Klonopin); clorazepate (Tranxene); diazepam (Valium); lorazepam (Ativan); oxazepam (Serax); and prazepam (Centrax). Antispasmodic medications include but are not limited to carmazepine (Tegretol); clonazepam (Klonopin); ethosuximide (Zarontin); ethotoin (Peganone); fosphenytoin (Cerebyx); gabapentin (Neurontin); lamotrigine (Lamictal); mephenytoin (Mesantoin); phenobarbital (Luminol, Solfoton); phenytoin (Dilantin); primidone (Mysoline); toiramate (Topamax); valproic acid (Depakene); divalproex sodium (Depakote, Depakote Sprinkles); and Gabapentin (Neurontin). Stimulants include but are not limited to dextroamphetamine sulfate (Das, Dexampex, Dexedrine, Dexedrine Spansules, Dextrostat, Ferndex, Oxydess); dextroamphetamine/amphetamine (Adderall); methamphetamine (MTH); methylphenidate hydrochloride (Ritalin); and pemoline (Cyclert); and phenylpropanolamine (PPA). Atypical neuroleptics include but are not limited to clozapine (Clozaril); olanzapine (Zyprexa); risperidone (Risperdal); quetiapine (Seroquel); and ziprasidone (Zeldox).

The compounds of the invention can be administered in combination with one or more minerals, such as, but not limited to, iron, calcium, potassium, zinc, manganese, phosphorous, chromium, magnesium, manganese, molybdenum, tin, nickel, sulfur, selenium, copper, cobalt, chloride, fluoride, and iodine. The minerals may be administered in large or trace amounts. The compounds can be administered together with the minerals in one formulation, or in different formulations.

When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following non-limiting example.

Example

Screening Compounds of the Invention in Human Dermal Fibroblasts from Autistic Patients A screen was perforated to identify compounds effective for the amelioration of ASD. Test samples, and solvent controls were tested for their ability to rescue ASD fibroblasts stressed by addition of L-buthionine-(S,R)-sulfoximine (BSO).

MEM (a medium enriched in amino acids and vitamins, catalog no. Gibco 11965) and Fetal Calf Serum were obtained from Invitrogen. Basic fibroblast growth factor and epidermal growth factor were purchased from PeproTech. Penicillin-streptomycin-glutamine mix, L-buthionine (S,R)-sulfoximine, and insulin from bovine pancreas were purchased from Sigma. Calcein AM was purchased from Molecular Probes. Cell culture medium (ATP) was made by combining 75 ml Fetal Calf Serum, 100 U/ml penicillin, 100 µg/ml streptomycin, 2 mM glutamine, 10 ng/ml EGF, and 10 ng/ml bFGF; MEM EBS was added to make the volume up to 500 ml. A 10 mM BSO solution was prepared by dissolving 444 mg BSO in 200 ml of medium with subsequent filter-sterilization. During the course of the experiments, this solution was stored at +4° C. The cells were obtained from Dr. J. M. Shoffner, Medical Neurogenetics, Atlanta, Ga. and were grown in 10 cm tissue culture plates. Every week, they were split at a 1:3 ratio.

The samples were supplied in 1.5 ml glass vials. The compounds were diluted with DMSO, ethanol or PBS to result in a 5 mM stock solution. Once dissolved, they were stored at −20° C.

The samples were screened according to the following protocol:

A culture with ASD fibroblasts was started from a 1 ml vial with approximately 500,000 cells stored in liquid nitrogen. Cells were propagated in 10 cm cell culture dishes by splitting every week in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 µl medium with 3,000 cells/well. The remaining cells were distributed in 10 cm cell culture plates (500,000 cells/plate) for propagation. The plates were incubated overnight at 37° C. in an atmosphere with 95% humidity and 5% $CO_2$ to allow attachment of the cells to the culture plate.

MTP medium (243 µl) was added to a well of the microtiter plate. The test compounds were unfrozen, and 7.5 µl of a 5 mM stock solution was dissolved in the well containing 243 µl medium, resulting in a 150 µM master solution. Serial dilutions from the master solution were made. The period between the single dilution steps was kept as short as possible (generally less than 1 second).

Plates were kept overnight in the cell culture incubator. The next day, 10 µl of a 10 mM BSO solution were added to the wells, resulting in a 1 mM final BSO concentration. Forty-eight hours later, three plates were examined under a phase-contrast microscope to verify that the cells in the 0% control (wells E1-H1) were clearly dead. The medium from all plates was discarded, and the remaining liquid was removed by gently tapping the plate inversed onto a paper towel.

100 µl of PBS containing 1.2 µM Calcein AM were then added to each well. The plates were incubated for 50-70 minutes at room temperature. After that time the PBS was discarded, the plate gently tapped on a paper towel and fluorescence (excitation/emission wavelengths of 485 nm and 525 nm, respectively) was read on a Gemini fluorescence reader. Data was imported into Microsoft Excel (EXCEL, is a registered trademark of Microsoft Corporation for a spreadsheet program) and used to calculate the $EC_{50}$ concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

Certain compounds of the present invention such as: 2,3,5-trimethyl-6-nonylcyclohexa-2,5-diene-1,4-dione and 2-(3-hydroxy-3,7,11,15-tetramethylhexadeca-6,10,14-trienyl)-3,5,6-trimethylcyclohexa-2,5-diene-1,4-dione and 2,3,5-trimethyl-6-nonylcyclohexa-2,5-diene-1,4-dione exhibited protection against ASD with an $EC_{50}$ of less than about 150 nM.

In general, the nomenclature used in this Application was generated with the help of naming package within the ChemOffice® version 11.0 suite of programs by CambridgeSoft Corp (Cambridge, Mass.).

What is claimed is:

1. A method of reducing one or more symptoms associated with, or of treating or suppressing a pervasive developmental disorder (PDD) or attention deficit/hyperactivity disorder (ADHD) in a patient in need thereof, comprising administering to the patient a therapeutically or physiologically effective amount of one or more compounds of Formula II,

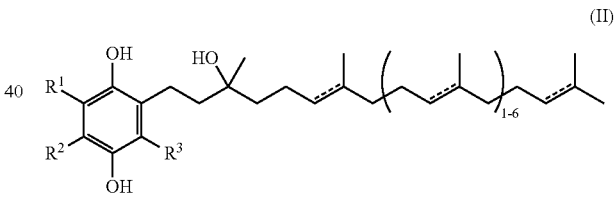

wherein,
the bonds indicated with a dashed line are independently single bonds or double bonds; and
$R^1$, $R^2$, and $R^3$ are independently selected from the group consisting of H, ($C_1$-$C_6$)alkyl, ($C_1$-$C_6$)haloalkyl, ($C_1$-$C_6$)alkoxy, halogen and CN;
or a stereoisomer, a mixture of stereoisomers, a solvate or a hydrate thereof.

2. The method according to claim 1, comprising administering a therapeutically or physiologically effective amount of one or more compounds of Formula IIa,

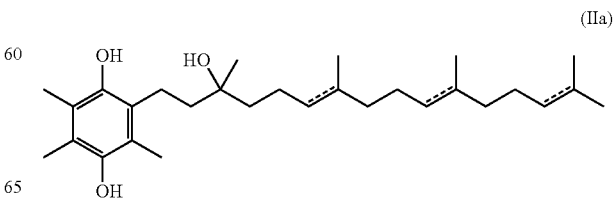

or a stereoisomer, a mixture of stereoisomers, a solvate or a hydrate thereof.

3. The method according to claim 1, wherein the method is for reducing one or more symptoms associated with, or for treating or suppressing a Pervasive Developmental Disorder (PDD).

4. The method according to claim 2, wherein the method is for reducing one or more symptoms associated with, or for treating or suppressing a Pervasive Developmental Disorder (PDD).

5. The method according to claim 1, wherein the method is for reducing one or more symptoms associated with, or for treating or suppressing attention deficit/hyperactivity disorder (ADHD).

6. The method according to claim 2, wherein the method is for reducing one or more symptoms associated with, or for treating or suppressing attention deficit/hyperactivity disorder (ADHD).

7. The method of claim 1, where the bonds indicated with a dashed line are all double bonds.

8. The method of claim 1, where the bonds indicated with a dashed line are all single bonds.

9. The method of claim 2, where the bonds indicated with a dashed line are all double bonds.

10. The method of claim 2, where the bonds indicated with a dashed line are all single bonds.

11. The method of claim 1, wherein $R^1$, $R^2$, and $R^3$ are independently $(C_1-C_4)$alkyl.

12. The method of claim 1, wherein $R^1$ and $R^2$ are independently $(C_1-C_4)$alkoxy, and $R^3$ is $(C_1-C_4)$alkyl.

13. The method of claim 9, wherein the one or more compounds are administered in the form of liposomes.

14. The method of claim 9, wherein the one or more compounds are administered in a medical food, functional food, food supplement, or dietary supplement.

15. The method according to claim 2, wherein the method is for reducing one or more symptoms associated with, or for treating or suppressing Rett syndrome.

16. The method according to claim 2, wherein the method is for reducing one or more symptoms associated with, or for treating or suppressing autism.

17. The method according to claim 9, wherein the method is for reducing one or more symptoms associated with, or for treating or suppressing a Pervasive Developmental Disorder (PDD).

18. The method according to claim 9, wherein the method is for reducing one or more symptoms associated with, or for treating or suppressing attention deficit/hyperactivity disorder (ADHD).

19. The method according to claim 9, wherein the method is for reducing one or more symptoms associated with, or for treating or suppressing autism.

20. The method according to claim 9, wherein the method is for reducing one or more symptoms associated with, or for treating or suppressing Rett syndrome.

* * * * *